(12) United States Patent
Van Pijkeren et al.

(10) Patent No.: US 10,898,552 B2
(45) Date of Patent: Jan. 26, 2021

(54) MICROORGANISMS AND METHODS FOR PRODUCING BIOLOGICS AND INTRODUCING BIOLOGICS TO SITES

(71) Applicant: WISCONSIN ALUMNI RESEARCH FOUNDATION, Madison, WI (US)

(72) Inventors: Jan Peter Van Pijkeren, Madison, WI (US); Jee-Hwan Oh, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

(21) Appl. No.: 16/654,400

(22) Filed: Oct. 16, 2019

(65) Prior Publication Data
US 2020/0030419 A1    Jan. 30, 2020

Related U.S. Application Data

(62) Division of application No. 15/819,936, filed on Nov. 21, 2017, now Pat. No. 10,463,719.

(60) Provisional application No. 62/424,905, filed on Nov. 21, 2016.

(51) Int. Cl.
| | | |
|---|---|---|
| *A61K 38/47* | (2006.01) | |
| *A61K 35/747* | (2015.01) | |
| *A61K 38/16* | (2006.01) | |
| *C07K 14/005* | (2006.01) | |
| *C12N 15/74* | (2006.01) | |
| *C12N 7/00* | (2006.01) | |
| *C12N 9/36* | (2006.01) | |

(52) U.S. Cl.
CPC ............ *A61K 38/47* (2013.01); *A61K 35/747* (2013.01); *A61K 38/162* (2013.01); *C07K 14/005* (2013.01); *C12N 7/00* (2013.01); *C12N 9/2462* (2013.01); *C12N 15/746* (2013.01); *C12N 2795/10033* (2013.01); *C12N 2830/002* (2013.01)

(58) Field of Classification Search
None
See application file for complete search history.

(56) References Cited

U.S. PATENT DOCUMENTS 10,376,563 B1 *  8/2019  Van Pijkeren ......... A61K 38/02
2010/0124558 A1   5/2010  Curtiss, III et al.

OTHER PUBLICATIONS

Alvarez-Sieiro P, Montalbán-López M, Mu D, Kuipers OP. Bacteriocins of lactic acid bacteria: extending the family. *Appl Microbiol Biotechnol.* 2016. 100(7):2939-51.
Bahey-El-Din M, Gahan CGM, Griffin BT. 2010. Lactococcus lactis as a cell factory for delivery of therapeutic proteins. Curr Gene Ther 10:34-45.
Barrangou R, van Pijkeren JP. Exploiting CRISPR-Cas immune systems for genome editing in bacteria. Curr Opin Biotechnol. Feb. 2016;37:61-8.
Becker SC, Dong S, Baker JR, Foster-Frey J, Pritchard DG, Donovan DM. 2009. LysK CHAP endopeptidase domain is required for lysis of live staphylococcal cells. FEMS Microbiol Lett 294:52-60.
Beisel CL, Gomaa AA, Barrangou R. 2014. A CRISPR design for next-generation antimicrobials. Genome Biol 15:516.
Bikard D, Euler CW, Jiang W, Nussenzweig PM, Goldberg GW, Duportet X, Fischetti VA, Marraffini LA. 2014.; Exploiting CRISPR-Cas nucleases to produce sequence-specific antimicrobials. Nat Biotech 32:1146-1150.
Borysowski J, Weber-Dabrowska B, Górski A.; Bacteriophage endolysins as a novel class of antibacterial agents. *Exp Biol Med* (Maywood). Apr. 2006; 231(4):366-77.
Britton, R. A.; Irwin, R.; Quach, D.; Schaefer, L.; Zhang, J.; Lee, T.; Parameswaran, N.; McCabe, L. R.; Probiotic L. reuteri Treatment Prevents Bone Loss in a Menopausal Ovariectomized Mouse Model. *J Cell Physiol* 2014, 229 (11), n/a—n/a DOI: 10.1002/jcp.24636.
Chambers, J. et al. Memorandum, Nucleic Acid and Peptide Claim Interpretation "A" and "The", USPTO Technology Center 1600, Dec. 29, 2005, 2 pages.
Chatel J-M, Pothelune L, Ah-Leung S, Corthier G, Wal J-M, Langella P. 2008; In vivo transfer of plasmid from food-grade transiting lactococci to murine epithelial cells. Gene Ther 15:1184-1190.
Cheng X, Zhang X, Pflugrath JW, Studier FW. 1994. The structure of bacteriophage T7 lysozyme, a zinc amidase and an inhibitor of T7 RNA polymerase. Proc Natl Acad Sci USA 91:4034-4038.
Citorik RJ, Mimee M, Lu TK. 2014. Sequence-specific antimicrobials using efficiently delivered RNA-guided nucleases. Nat Biotech 32:1141-1145.
Cotter PD, Ross RP, Hill C. 2013. Bacteriocins—a viable alternative to antibiotics? Nat Rev Microbiol 11:95-105.
Cronin, M.; Akin, A. R.; Collins, S. A.; Meganck, J.; Kim, J.-B.; Baban, C. K.; Joyce, S. A.; van Dam, G. M.; Zhang, N.; van Sinderen, D.; et al.; High resolution in vivo bioluminescent imaging for the study of bacterial tumour targeting. *PLoS ONE* 2012, 7 (1), e30940 DOI:10.1371/journal.pone.0030940.
De Azevedo M, Karczewski J, Lefèvre F, Azevedo V, Miyoshi A, Wells JM, Langella P, Chatel J-M. 2012.; In vitro and in vivo characterization of DNA delivery using recombinant Lactococcus lactis expressing a mutated form of L. monocytogenes Internalin A. BMC Microbiol 12:299.

(Continued)

*Primary Examiner* — Mary Maille Lyons
(74) *Attorney, Agent, or Firm* — Daniel A. Blasiole; DeWitt LLP

(57) ABSTRACT

Microorganisms comprising a maltose-inducible promoter and methods of use in producing biologics and introducing biologics to sites in a maltose-dependent manner. The microorganisms include a maltose-inducible promoter operably connected to a coding sequence of a biologic. The biologic may be a polypeptide or a nucleic acid. Polypeptide biologics may include lytic proteins and/or secreted proteins. Nucleic acid biologics may include antisense RNA, other types of RNA, or other types of nucleic acids. The microorganisms can be used to produce the biologics and/or introduce the biologics to in vitro or in vivo sites in a maltose-dependent manner. The microorganisms can also be used in maltose-dependent gene silencing.

9 Claims, 7 Drawing Sheets

Specification includes a Sequence Listing.

(56) References Cited

OTHER PUBLICATIONS

De Ruyter, P. G.; Kuipers, O. P.; Meijer, W. C.; de Vos, W. M. Food-grade controlled lysis of *Lactococcus lactis* for accelerated cheese ripening. *Nat Biotech* 1997, 15 (10), 976-979 DOI:10.1038/nbt1097-976.

De Weirdt R, Crabbé A, Roos S, Vollenweider S, Lacroix C, van Pijkeren J-P, Britton RA, Sarker S, Van de Wiele T, Nickerson CA. 2012.; Glycerol Supplementation Enhances L. reuteri's Protective Effect against S. Typhimurium Colonization in a 3-D Model of Colonic Epithelium. PLoS ONE 7:e37116.

Dishisha T, Pereyra LP, Pyo S-H, Britton RA, Hatti-Kaul R. 2014. Flux analysis of the Lactobacillus reuteri propanediol-utilization pathway for production of 3-hydroxypropionaldehyde, 3-hydroxypropionic acid and 1,3-propanediol from glycerol. Microb Cell Fact 13:76.

Doleyres Y, Beck P, Vollenweider S, Lacroix C. 2005.; Production of 3-hydroxypropionaldehyde using a two-step process with Lactobacillus reuteri. Appl Microbiol Biotechnol 68:467-474.

Eaton, K. A.; Honkala, A.; Auchtung, T. A.; Britton, R. A.; Probiotic *Lactobacillus reuteri* Ameliorates Disease Due to Enterohemorrhagic *Escherichia coli* in Germfree Mice. *Infect Immun* 2011, 79 (1), 185-191 DOI: 10.1128/IAI.00880-10.

Elzagheid, A.; Algars, A.; Bendardaf, R.; Lamlum, H.; Ristamaki, R.; Collan, Y.; Syrjanen, K.; Pyrhonen, S.; E-cadherin expression pattern in primary colorectal carcinomas and their metastases reflects disease outcome. *World J Gastroenterol* 2006, 12 (27), 4304-4309.

Feliza A. Bourguet, Brian E. Souza, Angela K. Hinz, Matthew A. Coleman, and Paul J. Jackson. Characterization of a Novel Lytic Protein Encoded by the *Bacillus cereus* E33L Gene ampD as a *Bacillus anthracis* Antimicrobial Protein. *Appl Environ Microbiol.* Apr. 2012; 78(8): 3025-3027.

Field D, Begley M, O'Connor PM, Daly Kzm, Hugenholtz F, Cotter PD, Hill C, Ross RP. 2012. Bioengineered Nisin Derivatives with Enhanced Activity against Both Gram Positive and Gram Negative Pathogens. PLoS ONE 7:e46884.

Field D, Connor PMO, Cotter PD, Hill C, Ross RP. 2008. The generation of nisin variants with enhanced activity against specific gram-positive pathogens.—PubMed—NCBI. Mol Microbiol 69:218-23.

Fischetti VA. 2004. The use of phage lytic enzymes to control bacterial infections, p. 321-334 In Kutter E, Sulakvelidze A, editors. (ed). Bacteriophages: biology and applications. CRC Press, Boca Raton, FL.

Fischetti VA. 2010. Bacteriophage Lysins: the Ultimate Enzybiotic; Enzybiotics. John Wiley & Sons, Inc., Hoboken, NJ, USA.

Fogel, M. R.; Gray, G. M. Starch hydrolysis in man: an intraluminal process not requiring membrane digestion. *J Appl Physiol* 1973, 35 (2), 263-267.

Frese, S. A.; Hutkins, R. W.; Walter, J. Comparison of the Colonization Ability of Autochthonous and Allochthonous Strains of Lactobacilli in the Human Gastrointestinal Tract. *Advances in Microbiology* 2012, 02 (03), 399-409 DOI: 10.4236/aim.2012.23051.

Gibson DG, Young L, Chuang R-Y, Venter JC, Hutchison CA, Smith HO. 2009. Enzymatic assembly of DNA molecules up to several hundred kilobases. Nat Meth 6:343-345.

Gomaa AA, Klumpe HE, Luo ML, Selle K, Barrangou R, Beisel CL. 2014.

Programmable Removal of Bacterial Strains by Use of Genome-Targeting CRISPR-Cas Systems. mBio 5:e00928-13.

Good L, Stach JE. Synthetic RNA silencing in bacteria—antimicrobial discovery and resistance breaking. Front Microbiol. Sep. 12, 2011;2:185.

Green et al., Molecular Cloning: A Laboratory Manual, 4th ed., Cold Spring Harbor Laboratory Press, 2012.

Guimarães V, Innocentin S, Chatel J-M, Lefèvre F, Langella P, Azevedo V, 582 Miyoshi A. 2009. A new plasmid vector for DNA delivery using lactococci. Genet Vaccines Ther 7:4.

Guimarãdes, V. D.; Gabriel, J. E.; Lefèvre, F.; Cabanes, D.; Gruss, A.; Cossart, P.; Azevedo, V.; Langella, P. Internalin-expressing *Lactococcus lactis* is able to invade small intestine of guinea pigs and deliver DNA into mammalian epithelial cells. *Microbes Infect* 2005, 7 (5-6), 836-844 DOI: 10.1016/j.micinf.2005.02.012.

Jacobs C, Huang LJ, Bartowsky E, Normark S, Park JT. Bacterial cell wall recycling provides cytosolic muropeptides as effectors for beta-lactamase induction. EMBO J. Oct. 3, 1994; 13(19):4684-94.

Jacobs C, Joris B, Jamin M, Klarsov K, Van Beeumen J, Mengin-Lecreulx D, van Heijenoort J, Park JT, Normark S, Frèere JM.; AmpD, essential for both beta-lactamase regulation and cell wall recycling, is a novel cytosolic N-acetylmuramyl-L-alanine amidase. *Mol Microbiol.* Feb. 1995; 15(3):553-9.

Komminenti S, Bretl DJ, Lam V, Chakraborty R, Hayward M, Simpson P, Cao Y, Bousounis P, Kristich CJ, Salzman NH. 2015.; Bacteriocin production augments niche competition by enterococci in the mammalian GI tract. Nature 526:719-722.

Lecuit, M.; Ohayon, H.; Braun, L.; Mengaud, J.; Cossart, P. Internalin of *Listeria monocytogenes* with an intact leucine-rich repeat region is sufficient to promote internalization. *Infect Immun* 1997, 65 (12), 5309-5319.

Liu, Y.; Fatheree, N. Y.; Mangalat, N.; Rhoads, J. M. Human-derived probiotic *Lactobacillus reuteri* strains differentially reduce intestinal inflammation. *Am J Physiol Gastrointest Liver Physiol* 2010, 299 (5), G1087-G1096 DOI: 10.1152/ajpgi.00124.2010.

Loessner MJ, Kramer K, Ebel F, Scherer S.; C-terminal domains of *Listeria monocytogenes* bacteriophage murein hydrolases determine specific recognition and high-affinity binding to bacterial cell wall carbohydrates. Mol Microbiol. Apr. 2002; 44(2):335-49.

Loessner MJ.; Bacteriophage endolysins—current state of research and applications. Curr Opin Microbiol. Aug. 2005; 8(4):480-7.

López R, García E, García P, Garcia JL. The pneumococcal cell wall degrading enzymes: a modular design to create new lysins? *Microb Drug Resist.* 1997; 3(2):199-211.

Navarre WW, Ton-That H, Faull KF, Schneewind O. 1999; Multiple Enzymatic Activities of the Murein Hydrolase from Staphylococcal Phage φ11. Journal of Biological Chemistry 274:15847-15856.

Nelson D, Schuch R, Chahales P, Zhu S, Fischetti VA. 2006; PlyC: A multimeric bacteriophage lysin. Proc Natl Acad Sci USA 103:10765-10770.

Nicoletti M, Bertani G. 1983. DNA fusion product of phage P2 with plasmid pBR322: A new phasmid. Mol Gen Genet 189:343-347.

Oh JH, van Pijkeren JP. CRISPR-Cas9-assisted recombineering in *Lactobacillus reuteri*. Nucleic Acids Res. 2014;42(17):e131.

Oh, P. L.; Benson, A. K.; Peterson, D. A.; Patil, P. B.; Moriyama, E. N.; Roos, S.; Walter, J. Diversification of the gut symbiont *Lactobacillus reuteri* as a result of host-driven evolution. *ISME J* 2010, 4 (3), 377-387 DOI: 10.1038/ismej.2009.123.

Paez-Espino D, Morovic W, Sun CL, Thomas BC, Ueda K-I, Stahl B, Barrangou R, Banfield JF. 2013; Strong bias in the bacterial CRISPR elements that confer immunity to phage. Nat Comms 4:1430-1430.

Pálffy, R.; Gardlíik, R.; Hodosy, J.; Behuliak, M.; Resko, P.; Radvánsky, J.; Celec, P.; Bacteria in gene therapy: bactofection versus alternative gene therapy. Gene Ther 2006, 13 (2), 101-105 doi:10.1038/sj.gt.3302635.

Riboulet-Bisson E, Sturme MHJ, Jeffery IB, O'Donnell MM, Neville BA, Forde BM, Claesson MJ, Harris H, Gardiner GE, Casey PG, Lawlor PG, O'Toole PW, Ross RP. 2012; Effect of Lactobacillus salivarius Bacteriocin Abp118 on the Mouse and Pig Intestinal Microbiota. PLoS ONE 7:e31113.

Riedel, C. U.; Monk, I. R.; Casey, P. G.; Morrissey, D.; O'Sullivan, G. C.; Tangney, M.; Hill, C.; Gahan, C. G. M. Improved luciferase tagging system for *Listeria monocytogenes* allows real-time monitoring in vivo and in vitro. *Appl Environ Microbiol* 2007, 73 (9), 3091-3094 DOI:10.1128/AEM.02940-06.

Robert S, Steidler L. 2014. Recombinant Lactococcus lactis can make the difference in antigen-specific immune tolerance induction, the Type 1 Diabetes case. Microb Cell Fact 13:S11.

Schaefer L, Auchtung TA, Hermans KWe, Whitehead D, Borhan B, Britton RA. 2010. The antimicrobial compound reuterin (3-hydroxypropionaldehyde) induces oxidative stress via interaction with thiol groups. Microbiology 156:1589-1599.

(56) References Cited

OTHER PUBLICATIONS

Sheehan MM, Stanley E, Fitzgerald GF, van Sinderen D. 1999. Identification and characterization of a lysis module present in a large proportion of bacteriophages infecting Streptococcus thermophilus. Appl Environ Microbiol 65:569-577.

Shi, Y.; Yan, Y.; Ji, W.; Bin Du; Meng, X.; Wang, H.; Sun, J. Characterization and determination of holin protein of *Streptococcus suis* bacteriophage SMP in heterologous host. *Virol J* 2012, 9 (1), 70-70 DOI: 10.1186/1743-422X-9-70.

Spinler JK, Taweechotipatr M, Rognerud CL, Ou CN, Tumwasorn S, Versalovic J. 2008. Human-derived probiotic Lactobacillus reuteri demonstrate antimicrobial activities targting diverse enteric bacterial pathogens. Anaerobe 14:166-171.

Steidler L, Hans W, Schotte L, Neirynck S, Obermeier F, Falk W, Fiers W, 574 Remaut E. 2000. Treatment of Murine Colitis by Lactococcus lactis Secreting Interleukin-10. Science 289:1352-1355.

Sørvig, Elisabeth, et al. "High-level, inducible gene expression in Lactobacillus sakei and Lactobacillus plantarum using versatile expression vectors." *Microbiology* 151.7 (2005): 2439-2449.

Sulakvelidze, Alexander; Alavidze, Zemphira; and J. Glenn Morris, Jr. Bacteriophage Therapy. *Antimicrob Agents Chemother.* 2001, 45(3): 649-659).

Summers WC. Bacteriophage therapy. *Annu Rev Microbiol.* 2001; 55:437-51.

Sznol, M.; Lin, S. L.; Bermudes, D.; Zheng, L.-M.; King, I. Use of preferentially replicating bacteria for the treatment of cancer. *Journal of Clinical Investigation* 2000, 105 (8), 1027-1030 DOI:10.1172/JCI9818.

Talarico TL, Casas IA, Chung TC, Dobrogosz WJ. 1988. Production and isolation of reuterin, a growth inhibitor produced by Lactobacillus reuteri. Antimicrob Agents Chemother 32:1854-185.

Tannock, G. W.; Wilson, C. M.; Loach, D.; Cook, G. M.; Eason, J.; O'Toole, P. W.; Holtrop, G.; Lawley, B. Resource partitioning in relation to cohabitation of *Lactobacillus* species in the mouse forestomach. *ISME J* 2011, 6 (5), 927-938 DOI: 10.1038/ismej.2011.161.

Thomas, C. M.; Hong, T.; van Pijkeren, J.P.; Hemarajata, P.; Trinh, D. V.; Hu, W.; Britton, R. A.; Kalkum, M.; Versalovic, J.; Histamine Derived from Probiotic *Lactobacillus reuteri* Suppresses TNF via Modulation of PKA and ERK Signaling. *PLoS ONE* 2012, 7 (2), e31951 DOI:10.1371/journal.pone.0037116.g006.

Van Pijkeren JP, Britton RA. High efficiency recombineering in lactic acid bacteria. *Nucleic Acids Res.* May 2012;40(10):e76.

Van Pijkeren J-P, Neoh KM, Sirias D, Findley AS, Britton RA. 2012. Exploring optimization parameters to increase ssDNA recombineering in Lactococcus lactis and Lactobacillus reuteri. Bioengineered 3:209-217.

Van Pijkeren, J.P.; Britton, R. A. Precision genome engineering in lactic acid bacteria. *Microb Cell Fact* 2014, 13 Suppl 1, S10-S10 DOI:10.1186/1475-2859-13-S1-S10.

Van Pijkeren, J.P.; Morrissey, D.; Monk, I. R.; Cronin, M.; Rajendran, S.; O'Sullivan, G. C.; Gahan, C. G. M.; Tangney, M. A novel *Listeria monocytogenes*-based DNA delivery system for cancer gene therapy. *Hum. Gene Ther.* 2010, 21 (4), 405-416 DOI: 10.1089/hum.2009.022.

Wang IN, Smith DL, Young R. 2000. Holins: the protein clocks of bacteriophage infections. Annual Reviews in Microbiology.

Wells M. et al. Lactococcus lactis: high-level expression of tetanus toxin fragment C and protection against lethal challenge. *Mol. Microbiol.*, 8 (1993), pp. 1155-1162.

Yang et al., Construction and characterization of a novel maltose inducible expression vector in Bacillus subtilis. *Biotechnology Letters* (2006) 28:1713-1718.

Zhang Y, Eigenbrot C, Zhou L, Shia S, Li W, Quan C, Tom J, Moran P, Di Lello P, Skelton NJ, Kong-Beltran M, Peterson A, Kirchhofer D. Identification of a small peptide that inhibits PCSK9 protein binding to the low density lippprotein receptor. *J. Biol Chem.* Jan. 10, 2014;29(2):942-55.

Zhou, Y.; Liang, Y.; Lynch, K. H.; Dennis, J. J.; Wishart, D. S. Phast: A Fast Phage Search Tool. 2011, 39 (suppl), W347-W352 DOI:10/1093/nar/gkr485.

\* cited by examiner

MICROORGANISMS AND METHODS FOR PRODUCING BIOLOGICS AND INTRODUCING BIOLOGICS TO SITES

FIELD OF THE INVENTION

The invention is directed to microorganisms and methods for producing biologics and introducing biologics to sites, including in vivo sites such as the gastrointestinal tract or in vitro sites.

BACKGROUND

The application of microorganisms for in situ delivery of therapeutics was first demonstrated by (Steidler et al. 2000) with lactic acid bacteria. The cheese bacterium *Lactococcus lactis* was engineered to secrete murine interleukin-10 (mIL10). Oral administration of the recombinant lactic acid bacterium significantly reduced intestinal inflammation in two mouse models of disease. The authors demonstrated mIL-10 was detected in the colon of $IL10^{-/-}$ mice and that the therapeutic effect was obtained following de novo synthesis of IL-10 by *L. lactis* during gastrointestinal (GI) transit. Since then, the *L. lactis* workhorse has been exploited to deliver a variety of recombinant proteins (Bahey-El-Din et al. 2010, Robert et al., 2014) and DNA (Guimarães et al. 2009, Chatel et al. 2008, de Azevedo et al., 2012), and has paved the way to harness other microbes as delivery vehicles. In particular, engineering food-grade microorganisms that can survive passage through the gastrointestinal tract, and naturally encode health-promoting properties, collectively provides a promising platform to deliver biologics of interest.

There are at least two challenges, however, to using microorganisms as biologic delivery vehicles. A first challenge is obtaining specificity in the delivery of biologics at therapeutic amounts, either with respect to particular sites in the body or within particular timeframes after administration. A second challenge is biologically containing the microorganisms. Biologic delivery vehicles that address these challenges are needed.

SUMMARY OF THE INVENTION

The present invention addresses the aforementioned challenges. The present invention provides microorganisms and methods for introducing biologics to a site upon stimulation with an environmental cue. The microorganisms of the invention employ a maltose-inducible promoter to stimulate production and/or release of biologics at the site upon exposure to maltose. Accordingly, the microorganisms can be used as a delivery platform to introduce biologics to sites that have a sufficient amount of maltose present to stimulate production and/or release of the biologics. The microorganisms can also be used as a delivery platform to deliver biologics to sites that do not have a sufficient amount of maltose present to stimulate production and/or release of the biologics. This can be done by "priming" the microorganisms with maltose prior to introducing the microorganisms to the site. The priming induces transcription and thereby permits production and/or release of biologics at later points in time to sites having no or low concentrations of maltose.

In some versions of the invention, the microorganisms are used as delivery vehicles to introduce biologics to in vivo sites, such as the gastrointestinal tract. The microorganism can be administered to the gastrointestinal tract orally or by other routes. Maltose present in the gastrointestinal tract simulates production and/or release of the biologics therein. To help induce production and/or release of the biologics, maltose levels in the gastrointestinal tract can be increased by administering maltose or a maltose precursor, such as starch, to the gastrointestinal tract. Alternatively or additionally, the microorganisms can be exposed to a maltose-rich medium to induce transcription prior to being administered to the gastrointestinal tract.

In other versions of the invention, the microorganisms are used to produce biologics in vitro. The microorganisms can be cultured in the presence of a sufficient amount of maltose present to stimulate product and/or release of the biologics.

The microorganisms of the invention can be configured to introduce biologics to a site in any of a number of formats. In some versions, the microorganisms are configured to secrete a secretable biologic in a maltose-dependent manner. In these versions, production of the secretable biologic is dependent on expression of one or more genes controlled by the maltose-inducible promoter such that the secretable biologic is produced and secreted upon exposure to maltose.

In other versions, the microorganisms are configured to constitutively produce a therapeutic biologic intracellularly but release the therapeutic biologic primarily in a maltose-dependent manner. In these versions, the microorganisms may comprise a maltose-dependent promoter operably connected to a nucleic acid sequence encoding a lytic protein that promotes lysis of the microorganism upon exposure to maltose. Exposure to maltose drives expression of the lytic protein, induces lysis of the microorganism, and facilitates release of the biologic.

In yet other versions, the microorganisms are configured both to produce a therapeutic biologic and to induce lysis in a maltose-dependent manner. In these versions, production of the biologic is dependent on expression of one or more genes controlled by the maltose-inducible promoter such that the biologic is produced upon exposure to maltose. The microorganisms also comprise a maltose-dependent promoter operably connected to a nucleic acid sequence encoding a lytic protein that promotes lysis of the microorganism upon exposure to maltose. Exposure to maltose drives expression of the lytic protein, induces lysis of the microorganism, and facilitates release of the biologic. There is typically a lag between induction of the lytic protein and cell lysis, which leaves time for intracellular production of the biologic before lysis.

In some versions of the invention, the microorganisms are configured to produce a biologic in a maltose-dependent manner regardless of whether or not the microorganism is configured for lysis.

The objects and advantages of the invention will appear more fully from the following detailed description of the preferred embodiment of the invention made in conjunction with the accompanying drawings.

DETAILED DESCRIPTION OF THE INVENTION

Figure 1:
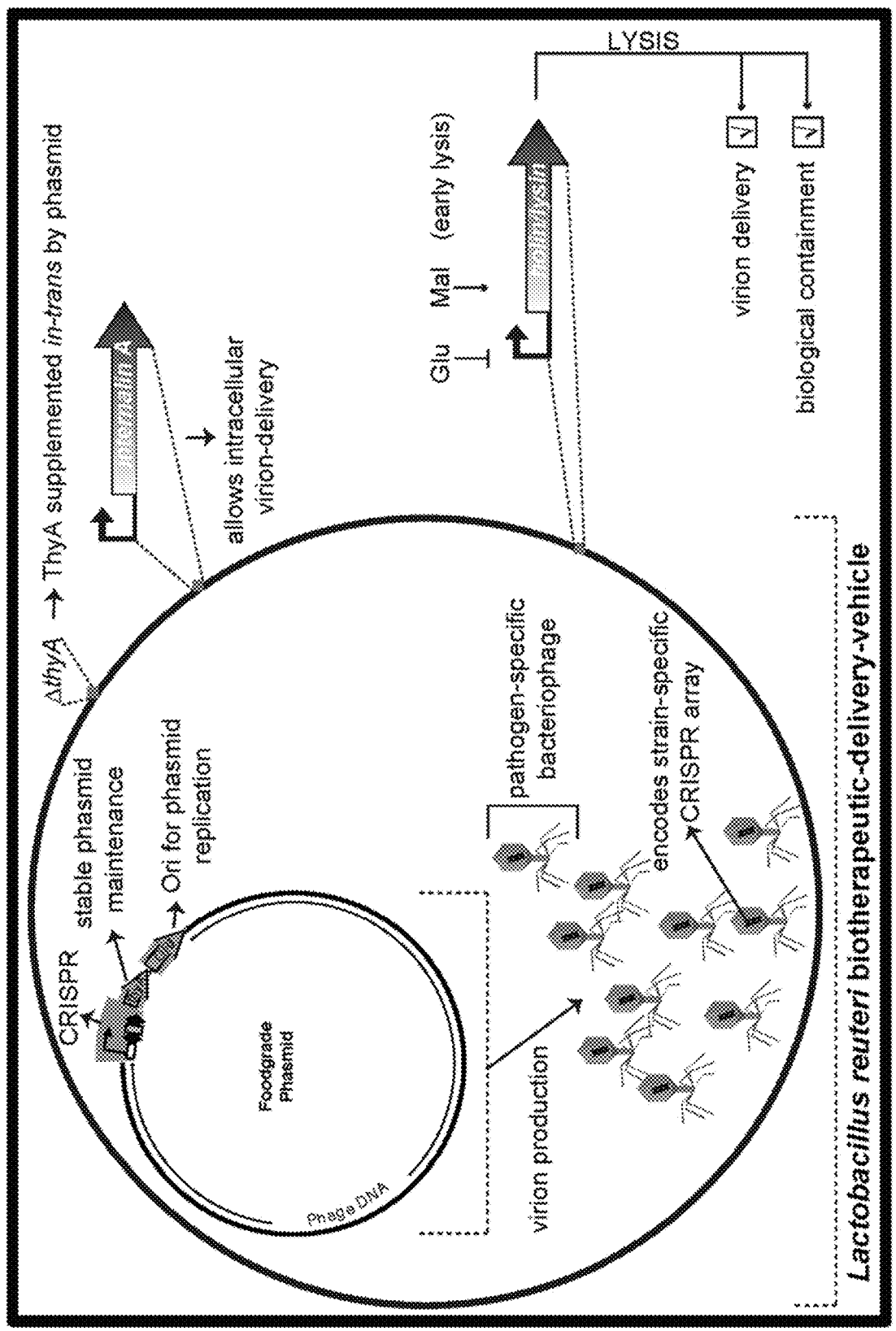
FIG. 1 shows a schema outlining an exemplary version of the invention, wherein a microorganism is modified for use as a biologic delivery vehicle. The microorganism is a *Lactobacillus reuteri* that produces a pathogen-specific bacteriophage as an exemplary biologic and harbors a maltose (mal)-sensitive lytic protein gene (e.g., holin and/or lysin). Maltose exposure leads to expression of the lytic protein gene, which, in turn, causes lysis of the microorganism and release of the biologic into the surroundings.

The microorganisms of the invention may comprise bacteria or other types of microorganisms, such as yeast. Bacteria of the invention may include certain commensal or probiotic bacteria, non-commensal bacteria, and other types of bacteria. The bacteria may include non-pathogenic, Gram-positive bacteria capable of anaerobic growth. The bacteria in some cases are viable in the gastrointestinal tract of mammals. The bacteria may be food grade.

Exemplary bacteria of the invention include species of lactic acid bacteria (i.e., species of the order Lactobacillales), such as those from the genera *Lactobacillus, Leuconostoc, Pediococcus, Lactococcus, Streptococcus, Aerococcus, Carnobacterium, Enterococcus, Oenococcus, Fructobacillus, Sporolactobacillus, Tetragenococcus, Vagococcus,* and *Weissella*.

Exemplary bacteria more preferably include species of the *Lactobacillus* genus. Exemplary species from the *Lactobacillus* genus include *L. acetototerans, L. acidifarinae, L. acidipiscis, L. acidophilus, L. agilis, L. algidus, L. atimentarius, L. amytolyticus, L. amylophilus, L. amylotrophicus, L. amylovorus, L. animatis, L. antri, L. apodemi, L. aviarius, L. bifermentans, L. brevis, L. buchneri, L. camelliae, L. casei, L. catenaformis, L. ceti, L. coleohominis, L. collinoides, L. composti, L. concavus, L. coryniformis, L. crispatus, L. crustorum, L. curvatus, L. delbrueckii* subsp. *delbrueckii, L. delbrueckii* subsp. *butgaricus, L. delbrueckii* subsp. *lactis, L. dextrinicus, L. diolivorans, L. equi, L. equigenerosi, L. farraginis, L. farciminis, L. fermentum, L. fornicalis, L. fructivorans, L. frumenti, L. fuchuensis, L. gallinarum, L. gasseri, L. gastricus, L. ghanensis, L. graminis, L. hammesii, L. hamsteri, L. harbinensis, L. hayakitensis, L. helveticus, L. hitgardii, L. homohiochii, L. iners, L. ingluviei, L. intestinalis, L. jensenii, L. johnsonii, L. katixensis, L. kefiranofaciens, L. kefiri, L. kimchii, L. kitasatonis, L. kunkeei, L. leichmannii, L. lindneri, L. malefermentans, L. coati, L. manihotivorans, L. mindensis, L. mucosae, L. murinus, L. nagelii, L. namurensis, L. nantensis, L. oligofermentans, L. oris, L. panis, L. pantheris, L. parabrevis, L. parabuchneri, L. paracollinoides, L. parafarraginis, L. parakefiri, L. paratimentarius, L. paraplantarum, L. pentosus, L. perolens, L. plantarum, L. pontis, L. psittaci, L. rennini, L. reuteri, L. rhamnosus, L. rimae, L. rogosae, L. rossiae, L. ruminis, L. saerimneri, L. sakei, L. salivarius, L. sanfranciscensis, L. satsumensis, L. secaliphilus, L. sharpeae, L. siliginis, L. spicheri, L. suebicus, L. thailandensis, L. ultunensis, L. vaccinostercus, L. vaginalis, L. versmoldensis, L. vini, L. vitulinus, L. zeae,* and *L. zymae*.

A bacterium used in the following examples is *L. reuteri*. In addition to *L. reuteri*, other particularly preferred bacteria include *L. plantarum* (e.g., *L. plantarum* BAA-793), *L. rhamnosus* (e.g., *L. rhamnosus* GG (*L. rhamnosus* ATCC 53103)), *L. lactis* (e.g., *L. lactis* MG1363), and *L. casei*.

In some versions, the microorganism is a bacterium other than *L. reuteri* strain 100-23. In some versions, the microorganism is a lactic acid bacterium other than *L. reuteri* strain 100-23. In some versions, the microorganism is a *L. reuteri* strain other than *L. reuteri* strain 100-23.

The microorganism may be configured to produce a biologic. As used herein, "biologic" refers to any biologically active product capable of being produced by a microorganism. The biologic can be biologically active in vivo in any prokaryote or eukaryote or in vitro in any in vitro biochemical system. The biologic can have any activity, whether enzymatic, binding, structural, etc. The microorganism may be genetically modified to produce the biologic. Accordingly, the microorganism may have at least one genetic modification that results in the production of a biologic that it naturally does not make and/or results the increased production of a biologic that it naturally does make. For example, the microorganism may include a transgene (chromosomally integrated or on a non-chromosomal plasmid, etc.) encoding a gene product it does not naturally express or may contain a modified gene (e.g., a gene with a modified or heterologous promoter or other genetic element) that enhances production of a gene product that it naturally expresses.

The biologic may have any of a variety of biological functions in a subject in which the microorganism is introduced. The biologic preferably has a therapeutic effect on the subject. The biologic may target and promote growth of beneficial cells in the subject, may target and inhibit growth of deleterious cells in the subject, or may target certain cells for destruction. The biologic may alter gene expression in a cell or may affect the physiology, growth, or activity of a cell in any other manner. Biologics that have a therapeutic effect on the subject are referred to herein as "therapeutic biologics."

Examples of biologics capable of being made by the microorganism include carbohydrates, polypeptides, nucleic acids, or complexes of these substances, such as viruses, etc., small molecules, and metabolites.

Exemplary nucleic acid biologics include DNA and RNA. Preferred nucleic acid biologics include therapeutic nucleic acids. Nucleic acid biologics can generally be classified as nucleotides and nucleosides, oligonucleotides, or polynucleotides. Various types of nucleic acid biologics include oligonucleotides for antisense and antigene applications, DNA aptamers, antisense oligodeoxynucleotides, DNAzymes, DNA vaccines, RNA-based therapeutics, RNA aptamers, RNA Decoys, antisense RNA, ribozymes, small interfering RNAs, and microRNAs, among others.

Exemplary viruses include bacteriophages, including antimicrobial bacteriophages. See, for example, (Sulakvelidze et al. 2001, Summers 2001, Borysowski et al. 2006, and Fischetti 2004). Since their discovery nearly a century ago, bacteriophages have been exploited to kill select microbes, which can be attributed to production of holins and/or endolysins. Historically, bacteriophage therapy was mainly focused in Eastern Europe whereas in the US the wide application of antibiotics was preferred (Sulakvelidze et al. 2001). However, the emerging and rapidly expanding threat of antibiotic-resistance has led to a revival of the use of bacteriophages in therapy.

Exemplary antimicrobial bacteriophages include those employing the CRISPR-Cas system to specifically target certain bacteria. CRISPR-Cas can be repurposed for applications such as programmable antimicrobials (Gomaa et al. 2014). What renders CRISPR machines desirable for genome editing in eukaryotes, makes them lethal antimicrobials in prokaryotes (Beisel et al. 2014). The paucity of DNA repair mechanisms in bacteria compared to eukaryotes renders bacteria highly susceptible to DNA damage, including CRISPR-induced DNA breaks and nicks. Therefore, self-targeting CRISPR spacers are highly lethal, and selected against during accidental acquisition of spacers from the host chromosome (Paez-Espino et al. 2013). This provides the opportunity for repurposing endogenous or exogenous CRISPR-Cas systems for self-targeting in bacteria, as programmable and specific antimicrobials (Gomaa et al. 2014).

Type I and Type II CRISPR-Cas systems harnessing both native and heterologous Cas nucleases have been generated in vivo and in vitro (Gomaa et al. 2014, Bikard et al. 2014, Citorik et al. 2014). However, a primary challenge in employing this technology is in-situ delivery of the bacteriophages to sites in the body—especially in the gastrointestinal tract. The microorganisms provided herein provide a solution to this challenge. The microorganisms described herein can be engineered as Trojan horses for the local delivery of engineered bacteriophages that carry CRISPR-cassette for self-targeting in pathogenic bacteria. A hybrid between a plasmid and a bacteriophage can be engineered to yield a phasmid for heterogenic bacteriophage production in the microorganism. The generation of a phasmid was already demonstrated 3 decades ago by fusion of the E. coli bacteriophage P2 with plasmid pBR322 (Nicoletti et al. 1983). Replication of the phasmid can be established from either the plasmid replication proteins, or from the bacteriophage replication proteins. Regardless of the modus of replication, functional virions can be produced. With the development of high-throughput assembling technologies, such as Gibson assembly (Gibson et al. 2009), building synthetic DNA fragments such as phasmids containing double-stranded bacteriophage DNA are a suitable approach. A CRISPR-array specific for a pathogen to be targeted can be embedded in the bacteriophage genome for packaging (Bikard et al. 2014, Citorik et al. 2014). Once the phasmid is established in the probiotic, virions are produced in the cytosol. Release of the virions in situ can occur using the modules and mechanisms described herein (e.g., a maltose-inducible promoter fused to a lytic protein gene to lyse the microorganism and release the engineered virions). The released virions will inject the DNA in the target pathogen to deliver the CRISPR-array, which, when combined with the native Cas proteins, will yield strain-specific killing.

Suitable polypeptide biologics may include any polypeptide of interest. The polypeptide may have any of a number of amino acid chain lengths. In some versions, the polypeptide may have an amino acid chain length of from about 2 to about 2,000 amino acids, from about 2 to about 1,000 amino acids, from about 2 to about 500 amino acids, from about 3 to about 250 amino acids, or from about 3 to about 225 amino acids. The polypeptide may have a net positive charge at neutral pH, a net negative charge at neutral pH, or a net neutral charge at neutral pH. The polypeptide is preferably soluble in water. The polypeptide may form a globular or fibrous structure or may have an intrinsically disordered structure.

The polypeptide may have any of a number of functionalities. The polypeptide, for example, may be enzymatic or non-enzymatic. The polypeptide may be fluorescent or non-fluorescent. The polypeptide may be a cytokine, a hormone, an antibody, an antimicrobial peptide, and an antigenic peptide, among others.

Exemplary classes of cytokines include interleukins, lymphokines, monokines, interferons (IFNs), colony stimulating factors (CSFs), among others. Specific exemplary cytokines include IL-1 alpha (IL1a), IL-1 beta (IL1b), IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-35, IL-36, IFN-alpha, IFN-beta IFN-gamma, TNF-alpha, TNF-beta, CNTF (C-NTF), LIF, OSM (oncostatin-M), EPO (erythropoietin), G-CSF (GCSF), GM-CSF (GMCSF), M-CSF (MCSF), SCF, GH (growth hormone), PRL (prolactin), aFGF (FGF-acidic), bFGF (FGF-basic), INT-2, KGF (FGF7). EGF, TGF-alpha, TGF-beta, PDGF, betacellulin (BTC), SCDGF, amphiregulin, and HB-EG, among others.

Exemplary hormones include epinephrine, melatonin, triiodothyronine, thyroxine, amylin (or islet amyloid polypeptide), adiponectin, adrenocorticotropic hormone (or corticotropin), angiotensinogen, angiotensin, antidiuretic hormone (or vasopres sin, arginine vasopressin), atrial-natriuretic peptide (or atriopeptin), brain natriuretic peptide, calcitonin, cholecystokinin, corticotropin-releasing hormone, cortistatin, encephalin, endothelin, erythropoietin, follicle-stimulating hormone, galanin, gastric inhibitory polypeptide, gastrin, ghrelin, glucagon, glucagon-like peptide-1, gonadotropin-releasing hormone, growth hormone-releasing hormone, hepcidin, human chorionic gonadotropin, human placental lactogen, growth hormone, inhibin, insulin, insulin-like growth factor (or somatomedin), leptin, lipotropin, luteinizing hormone, melanocyte stimulating hormone, motilin, orexin, oxytocin, pancreatic polypeptide, parathyroid hormone, pituitary adenylate cyclase-activating peptide, prolactin, prolactin releasing hormone, relaxin, renin, secretin, somatostatin, thrombopoietin, thyroid-stimulating hormone (or thyrotropin), thyrotropin-releasing hormone, and vasoactive intestinal peptide, among others.

Other physiologically active peptides include tachykinin peptides, such as substance P, kassinin, neurokinin A, eledoisin, and neurokinin B; peptide PHI 27 (peptide histidine isoleucine 27); pancreatic polypeptide-related peptides, such as NPY (neuropeptide Y), PYY (peptide YY), and APP (avian pancreatic polypeptide); opioid peptides, such as proopiomelanocortin (POMC) peptides and prodynorphin peptides; AGG01; B-type natriuretic peptide (BNP); lactotripeptides; and peptides that inhibit PCSK9 (Zhang et al. 2014).

Exemplary antibodies include single-chain antibodies, single-domain antibodies (sdAbs), and single-chain variable fragments (scFvs).

Exemplary antimicrobial peptides include cathelicidins, defensins, protegrins, mastoparan, poneratoxin, cecropin, moricin, melittin, magainin, dermaseptin, nisin, and others. Other antimicrobial peptides include regIII-β and reg-III-γ, which are eukaryotic antimicrobial peptides produced in the intestine. Lactic acid bacteria are well known for their extensive heterogenic repertoire of antimicrobial compounds, including bacteriocins (Alvarez-Sieiro et al. 2016).

Other exemplary biologics include peptides that play a role in degrading bacterial cell walls, such as holins and lysins.

Other exemplary biologics include any of a number of antimicrobials produced (either naturally or via engineering) by microorganisms. Lactic acid bacteria, for example, are well-known for their extensive heterogenic repertoire of antimicrobial compounds, including bacteriocins (Alvarez-Sieiro et al. 2016). Bacteriocins are small ribosomally-synthesized peptides that can inhibit or kill bacteria. The functional diversity of this family of antimicrobials is large, which is illustrated by the fact that bacteriocins can collectively target a wide-array of Gram-negative and Gram-positive bacteria (Cotter et al. 2013).

Although narrow-spectrum bacteriocins may be preferential, the application of broad-spectrum bacteriocins may be useful to alleviate a bacterial infection of unknown source. Bacteriocin-mediated impact on the gut microbiota composition can be substantial. This was demonstrated for Abp118, a broad-spectrum bacteriocin produced by L. salivarius UCC118 (Riboulet-Bisson et al. 2012). By comparing the microbiota in mice and pigs between groups that were administrated with L. salivarius wild-type or L. salivariusΔabp118, it was confirmed that the presence of the bacteriocin-producing lactobacilli alters the gut microbiota composition without significance changes in microbial diversity. This study, and that of others (Kommineni et al. 2015), demonstrates that a bacteriocin-producing probiotic can eradicate select members of the gut microbiota, providing a rationale to engineer bacteriocins for enhanced efficacy.

One example of a useful bacteriocin is nisin, which is produced by select Lactococcus lactis strains and streptococci. The 372 basepair gene encoding nisin (nisA), one of the six natural nisin variants, was subjected to site-directed and saturation mutagenesis, and mutants were recovered that displayed enhanced activity against Gram-positive and Gram-negative pathogens (Field et al. 2008, Field et al. 2012). The above-described methodology was based on modification of a plasmid-encoded nisin by PCR. Recent developments now enable codon saturation mutagenesis in the chromosome. In L. reuteri, single-stranded DNA recombineering can be combined with CRISPR-Cas selection, which allows one-step codon saturation mutagenesis (Oh et al. 2014). A single transformation of an oligonucleotide containing the NNK motif (N=A/T/G/C and K=G/T) yielded a pool of recombinants in which a single codon was modified to encode for all 20 amino acids. These approaches can be multiplexed to accelerate the discovery of probiotics with enhanced anti-microbial activity.

Rather than using codon mutagenesis to identify novel anti-microbial variants, genetic engineering approaches can also be applied to enhance the production of the antimicrobial. This was previously demonstrated for reuterin, also known as 3-hydroxypropionaldehyde (3-HPA) (van Pijkeren and Neoh et al. 2012). Select L. reuteri strains produce reuterin as an intermediate during glycerol fermentation to produce 1,3-propanediol (Doleyres et al. 2005). Reuterin has a broad-spectrum activity (Spinler et al. 2008, De Weirdt et al. 2012, Talarico et al. 1988). The gene cluster responsible for 1,3-propanediol production (and thus reuterin) is the propanediol utilization (pdu) operon. By single-stranded DNA recombineering six bases were modified in the promoter region driving expression of the pdu operon. The recombinant strain produced more reuterin (Dishisha et al. 2014, van Pijkeren and Britton et al. 2012, van Pijkeren and Neoh et al. 2012), resulting in 3-fold increased killing efficacy of E. coli compared to the wild-type strain (van Pijkeren and Neoh et al. 2012). Also, deletion of the gene encoding 1,3-propanediol reductase, which is responsible for the conversion of reuterin to 1,3-propanediol, yielded approximately 4-fold more reuterin compared to the wild-type (Schaefer et al. 2010). A double mutant derivative in which increased expression of the pdu operon is combined with deletion of the 1,3-propanediol reductase gene can yield a tailored probiotic with superior in-vivo killing activity.

Preferred versions of the invention make use of a maltose-inducible promoter for introducing a biologic to a particular site. As used herein, "introduce" and its grammatical equivalents, when used in reference to an element such as a microorganism or a biologic, refers to any activity that results in the initial appearance or increased appearance of the element at the site. Introducing microorganisms to a site may comprise, for example, inoculating, administering, culturing, and growing the microorganism at that site. Introducing biologics to a site may comprise, for example, stimulating production of the biologics and/or release of the biologics at the site.

An exemplary maltose-inducible promoter is represented by SEQ ID NO:1, which is a maltose-inducible promoter found in L. reuteri:

```
                                    (SEQ ID NO: 1)
TACCAAGAATAACTTTCATCGTAAAAGGCAAGTAATTGAGGAAACTTGA

AGTTTTTCTCTATTACTTGCCTTCTTTATTTTATTAAGCTAAATATGTT

TTAAATAATTAACTATAACGGACCTGCTTGGCGGAAACTAAACAGTAAG

AACTTTAAATTATAAAAATCTGCAACCGTTTTCTAAAATTTTGCGCAAG

CGGTTGCGCAAAATTTTTAAATTTGATATTATTAATATTGCAATAATTC

ATGAAGCGCTTACAATAATCACAAGTGTCTTTTAGAACTATTTTATAAG

TTAAGGAGTTGTTAGCA
```

The maltose-inducible promoter represented by SEQ ID NO:1 or variants thereof are suitable for use in the present invention. Variants of SEQ ID NO:1 include sequences at least about 80% identical, at least about 83% identical, at least about 85% identical, at least about 87% identical, at least about 90% identical, at least about 83% identical, at least about 95% identical, at least about 97% identical, at least about 98% identical, or at least about 99% identical to SEQ ID NO:1

In some versions of the invention, the maltose-inducible promoter is operably connected to a coding sequence of a gene product. The maltose-inducible promoter can be operably connected to the coding sequence of any biologic described herein. As used herein, "gene product" refers to any product resulting from expression (e.g., transcription or transcription and translation) of a gene. The term "gene product" explicitly encompasses polypeptides as well as nucleic acids such as RNA (e.g., mRNA, pri-microRNA, pre-microRNA, microRNA, antisense RNA (asRNA) etc.) and DNA (cDNA). "Coding sequence" refers to a nucleic acid in the gene that encodes the gene product. The term "coding sequence" encompasses sequences that include codons that are ultimately transcribed and translated into polypeptides as well as sequences that do not include codons and/or are merely transcribed (e.g., antisense RNA, etc.). "Gene" refers to any collection of genetic elements involved in expressing a coding sequence and may include, in addition to the coding sequence, a promoter, a ribosomal binding site, an enhancer, etc. The term "gene" encompasses genetic elements that are transcribed into mRNA and translated into polypeptides as well as genetic elements that are merely transcribed into various types of RNA (e.g., microRNA, antisense RNA, etc.). "Promoter" refers to any nucleic acid that confers, activates, or enhances expression of an operably connected coding sequence. "Operably connected" generally refers to a connection of two genetic elements in a manner wherein one can operate on or have effects on the other. "Operably connected" used in reference to a promoter and a coding sequence refers to a connection between the promoter and the coding sequence such that the coding sequence is under transcriptional control of the promoter. For example, promoters are generally positioned 5' (upstream) of a coding sequence to be operably connected to the promoter. In the construction of heterologous promoter/coding sequence combinations, it is generally preferred to position the promoter at a distance from the transcription start site that is approximately the same as the distance between that promoter and the coding sequence it controls in its natural setting, i.e., in the gene from which the promoter is derived. As is known in the art, some variation in this distance can be accommodated without loss of promoter function.

In some versions of the invention, the maltose-inducible promoter is operably connected to the coding sequence of a lytic protein as a biologic. As used herein, "lytic protein" refers to any protein that causes or aids, either directly or indirectly, in the lysis of a microorganism. Operably connecting the maltose-inducible promoter to the coding sequence of a lytic protein induces lysis of the microorganism, release of the lytic protein, and release of any other biologics made by the microorganism in a maltose-dependent manner. Such release can occur, for example, in the gastrointestinal tract due to natural levels of maltose therein, or in other sites of the body with low levels of maltose due to maltose priming, as discussed in further detail below. Such release can also occur in vitro, whether in the presence of high levels of maltose or in the presence of low or no levels of maltose due to maltose priming.

Lytic proteins are well known in the art. A number of lytic proteins, for example, are found in bacteriophages and serve to lyse microorganisms during the lytic stages of the bacteriophage's life cycle. These include holins and lysins (Sheehan et al. 1999). During bacteriophage replication, biologically active lysins are present in the cytosol but require expression of a membrane protein, holin, to release the virions from the cell. When holin levels are optimal, the lysin can access the peptidoglycan layer for cleavage which leads to bacterial cell lysis (Wang et al. 2000). So far, five main groups of lysins have been identified that can be distinguished from one another based on the cleavage specificity of the different bonds within the peptidoglycan (Fischetti 2009). Structurally, lysins can comprise a single catalytic domain, which generally is typical for lysins derived from bacteriophages targeting Gram-negative bacteria (Cheng et al. 1994). Bacteriophages targeting Gram-positive bacteria typically encode lysins that contain multiple domains: a N-terminal catalytic domain and a C-terminal cell-wall binding domain (Nelson et al. 2006, Navarre et al. 1999). A few lysins have been identified that have three domains (Becker et al. 2009).

A number of other lytic proteins are native to the microorganisms themselves (Feliza et al. 2012, Jacobs et al. 1994, Jacobs et al. 1995, López et al. 1997). These lytic proteins may affect cell wall metabolism or introduce nicks in the cell wall. Five protein classes are differentiated by the wall component they attack (Loessner et al. 2005, Loessner et al. 2002).

In some versions of the invention, the microorganism is configured to constitutively express a lysin and to express a holin in a maltose-dependent manner. In some versions, the microorganism is configured to express both a lysin and a holin in a maltose-dependent manner.

In certain versions of the invention, maltose-dependent lysis of the microorganism serves to release one or more additional biologics made by the microorganism other than the lysis protein. The microorganism may naturally produce such additional biologics or may be genetically modified to produce or enhance production of the additional biologics. The one or more additional biologics may comprise any one or more of the biologics described herein or otherwise known in the art. The additional biologics may be produced in a maltose-dependent manner or in a maltose-independent manner. For example, a gene responsible for making the biologic, either directly or indirectly, can be controlled by a maltose-inducible promoter or with any other inducible or constitutive promoter. The maltose-inducible promoter may be operably connected to a coding sequence of an additional biologic itself such that production of the biologic is directly controlled by the maltose-inducible promoter. The maltose-inducible promoter may alternatively be operably connected to one or more coding sequences of factors responsible for producing an additional biologic such that production of the biologic is indirectly controlled by the maltose-inducible promoter. The additional biologics may be non-secreted biologics, meaning that the biologics may be substantially inhibited from being released from the microorganism until the microorganism is lysed.

In some versions of the invention, the microorganism is configured to produce a biologic in a maltose-dependent manner regardless of whether or not the biologic is ultimately released from the microorganism through lysis. For example, the maltose-inducible promoter may be operably connected to a gene product that is produced within the microorganism without substantial release therefrom. The gene product may be internally contained within the microorganism for an extended period of time. The gene product may include any gene product described herein, including any polypeptide and any nucleic acid. The produced gene products may have a functional effect on the microorganism.

The maltose-inducible promoter, for example, may be used for maltose-inducible gene silencing with the use of antisense RNA (asRNA). The antisense RNA may include cis-encoded asRNA or trans-encoded asRNA. Cis-encoded asRNA can be obtained by cloning the maltose-inducible promoter on the opposing DNA strand and in the opposite orientation of a gene of interest. Trans-encoded asRNA can be obtained by cloning the maltose-inducible promoter in front of an asRNA-producing coding sequence at a locus (elsewhere in the genome or from a plasmid, etc.) other than where the gene of interest resides.

Figure 7:
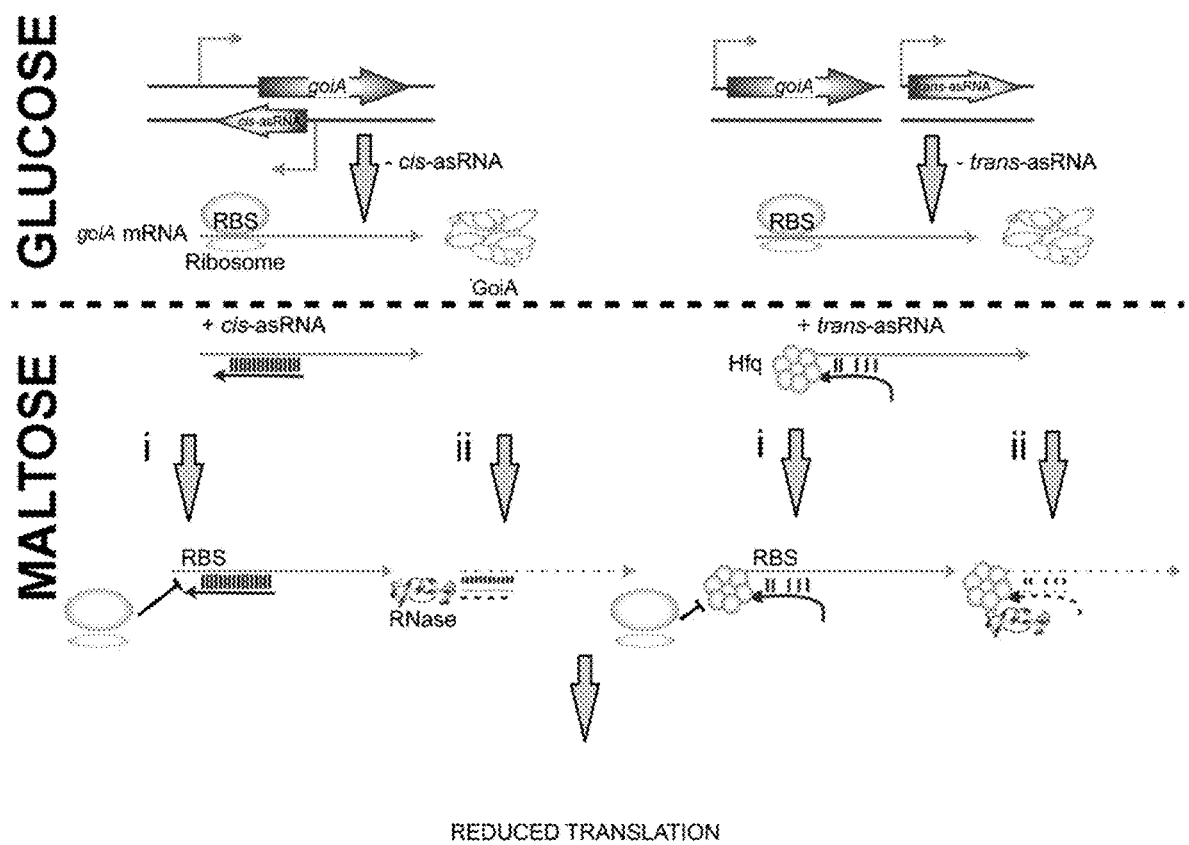
FIG. 7 depicts a schema showing maltose-inducible gene silencing in bacteria using antisense RNA (asRNA), specifically with cis-encoded asRNA and trans-encoded asRNA.

A schema showing maltose-inducible gene silencing using cis-encoded or trans-encoded asRNA is provided in FIG. 7. In the presence of glucose (top panel of FIG. 7), there is no production of cis-encoded (left side of FIG. 7) or trans-encoded (right side of FIG. 7) antisense RNA (asRNA). Thus, gene-of-interest (goiA) mRNA is produced which will lead to production of the protein (GoiA). Activation of the promoter by maltose (bottom panel in FIG. 7) leads to production of cis-encoded asRNA (left side of FIG. 7) or trans-encoded asRNA (right side of FIG. 7). In nature, and as depicted in the FIG. 7, trans-encoded asRNA has limited complementarity with the mRNA and requires the RNA chaperon Hfq to facilitate binding. However, the trans-encoded asRNA can be user-defined and is therefore not a limitation for the application of the maltose-inducible trans-encoded asRNA expression. Once the asRNA (cis- or trans-) is bound to the target mRNA, there are different processes that can contribute to reduce translation. This can be achieved through blocking binding to the ribosomal binding site (RBS) (i in FIG. 7), through RNase-mediated degradation of the mRNA:asRNA complex (ii in FIG. 7), or both. For further aspects of employing gene silencing with asRNA, see Good et al. 2011. One of skill in the art is readily capable of identifying antisense sequences for any gene of interest.

Any of the biologics made by the microorganism may be produced from a recombinant gene. "Recombinant" used in reference to a gene refers herein to a sequence of nucleic acids that are not naturally occurring in the genome of the microorganism. The non-naturally occurring sequence may include a recombination, substitution, deletion, or addition of one or more bases with respect to the nucleic acid sequence originally present in the natural genome of the bacterium. The recombinant gene may be incorporated into the chromosome of the microorganism or may be included on an extra-chromosomal plasmid. The extra-chromosomal plasmid may replicate at any copy number in the cell and, accordingly, be a single-copy plasmid, a low-copy plasmid, or a high-copy plasmid. The extra-chromosomal plasmid is preferably substantially stable within the microorganism. The rate of loss of the extra-chromosomal plasmid from the microorganism is preferably less than about 10% per generation, less than about 5% per generation, or less than about 1% per generation, wherein percent per generation refers to the percent of the population per generation in which the plasmid is lost.

In some versions, stability of an extrachromosomal plasmid in a microorganism is established by including an antibiotic marker on the plasmid and selecting for microorganisms harboring the plasmid with the antibiotic. Such selection can occur in vitro and in vivo. As administration of antibiotics can be undesired in some cases, stability of the extrachromosomal plasmid in the microorganism can be established in an antibiotic-independent manner. An exemplary method of establishing stability of the extrachromosomal plasmid in the microorganism in an antibiotic-independent manner is by inducing auxotrophy in the microorganism with respect to a factor limited or absent in its surroundings and including a gene that resolves that auxotrophy on the extrachromosomal plasmid. An example of this method is provided in the examples, in which thyA is deleted from *L. reuteri* but is included on an extrachromosomal plasmid harbored by the *L. reuteri*.

Figure 3:
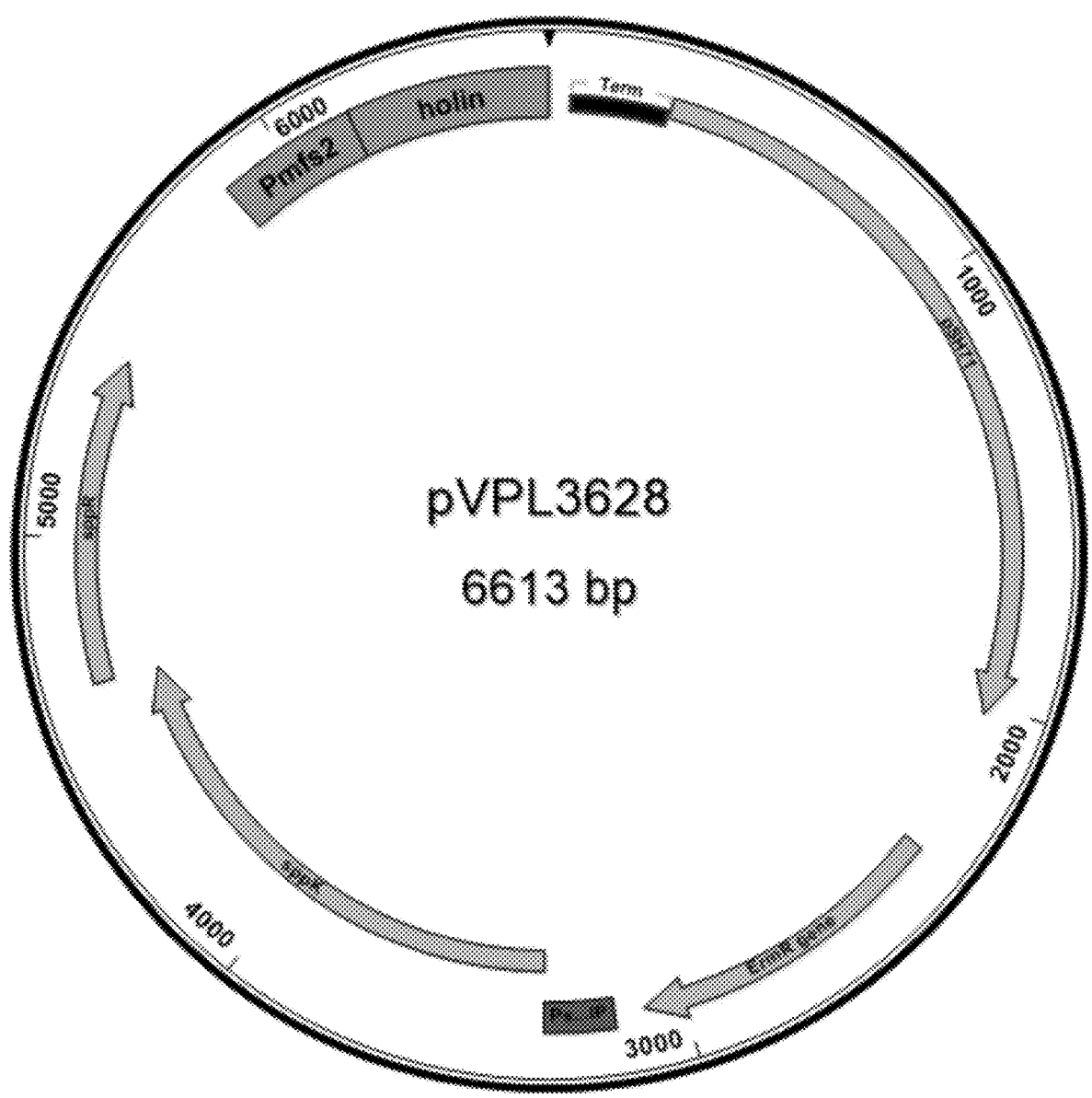
FIG. 3 shows a schema of an exemplary plasmid (pVPL3628) containing a maltose-inducible holin gene of the invention. "Pmfs2" indicates a maltose-inducible promoter. "Holin" indicates a holin coding sequence. "Term" indicates a transcriptional terminator sequence. "Erm$^R$ gene" indicates an erythromycin resistance marker. "pSH71" indicates a replication origin. "sspK" and "sspR" indicate a two component system. The replication origin (pSH71), the two component system (sspK, sspR), and the Erm$^R$ gene are from parent plasmid (pSIP411).

An exemplary extrachromosomal plasmid containing a recombinant, maltose-inducible gene for holin as a biologic is provided by SEQ ID NO:2, a schema of which is shown in FIG. 3:

(SEQ ID NO: 2)
TAATCTAGACTCGAGGAATTCGGTACCCCGGGTTCGAAGGCGCCAAGC

TTCAAATTACAGCACGTGTTGCTTTGATTGATAGCCAAAAAGCAGCAG

TTGATAAAGCAATTACTGATATTGCTGAAAAATTGTAATTTATAAATA

AAAATCACCTTTTAGAGGTGGTTTTTTTATTTATAAATTATTCGTTTG

ATTTCGCTTTCGATAGAACAATCAAAGCGAGAATAAGGAAGATAAATC

CCATAAGGGCGGGAGCAGAATGTCCGAGACTAATTCATGAGATCGATT

TTTTATTAAAACGTCTCAAAATCGTTTCTGAGACGTTTTAGCGTTTAT

TTCGTTTAGTTATCGGCATAATCGTTAAAACAGGCGTTATCGTAGCGT

AAAAGCCCTTGAGCGTAGCGTGCTTTGCAGCGAAGATGTTGTCTGTTA

GATTATGAAAGCCGATGACTGAATGAAATAATAAGCGCAGCGTCCTTC

TATTTCGGTTGGAGGAGGCTCAAGGGAGTTTGAGGGAATGAAATTCCC

TCATGGGTTTGATTTTAAAAATTGCTTGCAATTTTGCCGAGCGGTAGC

GCTGGAAAAATTTTTGAAAAAAATTTGGAATTTGGAAAAAAATGGGGG

GAAAGGAAGCGAATTTTGCTTCCGTACTACGACCCCCCATTAAGTGCC

GAGTGCCAATTTTTGTGCCAAAAACGCTCTATCCCAACTGGCTCAAGG

GTTTGAGGGGTTTTTCAATCGCCAACGAATCGCCAACGTTTTCGCCAA

CGTTTTTTATAAATCTATATTTAAGTAGCTTTATTGTTGTTTTATGA

TTACAAAGTGATACACTAATTTTATAAAATTATTTGATTGGAGTTTTT

TAAATGGTGATTTCAGAATCGAAAAAAAGAGTTATGATTTCTCTGACA

AAAGAGCAAGATAAAAAATTAACAGATATGGCGAAACAAAAAGGTTTT

TCAAAATCTGCGGTTGCGGCGTTAGCTATAGAAGAATATGCAAGAAAG

GAATCAGAATAAAAAAATAAGCGAAAGCTCGCGTTTTTAGAAGGATA

CGAGTTTTCGCTACTTGTTTTTGATAAGGTAATATATCATGGCTATTA

AATACTAAAGCTAGAAATTTTGGATTTTTATTATATCCTGACTCAATT

CCTAATGATTGGAAAGAAAAATTAGAGAGTTTGGGCGTATCTATGGCT

GTCAGTCCTTTACACGATATGGACGAAAAAAAAGATAAAGATACATGG

AATAGTAGTGATGTTATACGAAATGGAAAGCACTATAAAAAACCACAC

TATCACGTTATATATATTGCACGAAATCCTGTAACAATAGAAAGCGTT

AGGAACAAGATTAAGCGAAAATTGGGGAATAGTTCAGTTGCTCATGTT

GAGATACTTGATTATATCAAAGGTTCATATGAATATTTGACTCATGAA

TCAAAGGACGCTATTGCTAAGAATAAACATATATACGACAAAAAAGAT

ATTTTGAACATTAATGATTTTGATATTGACCGCTATATAACACTTGAT

GAAAGCCAAAAAAGAGAATTGAAGAATTTACTTTTAGATATAGTGGAT

GACTATAATTTGGTAAATACAAAAGATTTAATGGCTTTTATTCGCCTT

AGGGGAGCGGAGTTTGGAATTTTAAATACGAATGATGTAAAAGATATT

GTTTCAACAAACTCTAGCGCCTTTAGATTATGGTTTGAGGGCAATTAT

CAGTGTGGATATAGAGCAAGTTATGCAAAGGTTCTTGATGCTGAAACG

GGGGAAATAAAATGACAAACAAAGAAAAAGAGTTATTTGCTGAAAATG

AGGAATTAAAAAAAGAAATTAAGGACTTAAAAGAGCGTATTGAAAGAT

ACAGAGAAATGGAAGTTGAATTAAGTACAACAATAGATTTATTGAGAG

-continued

GAGGGATTATTGAATAAATAAAAGCCCCCCTGACGAAAGTCGAAGGGG
GCTTTTATTTTGGTTTGATGTTGCGATTAATAGCAATACGATTGCAAT
AAACAAAATGATCCCCTTAGAAGCAAACTTAAGAGTGTGTTGATAGTG
CATTATCTTAAAATTTTGTATAATAGGAATTGAAGTTAAATTAGATGC
TAAAAATAGGAATTGAAGTTAAATTAGATGCTAAAAATTTGTAATTAA
GAAGGAGGGATTCGTCATGTTGGTATTCCAAATGCGTAATGTAGATAA
AACATCTACTGTTTTGAAACAGACTAAAAACAGTGATTACGCAGATAA
ATAAATACGTTAGATTAATTCCTACCAGTGACTAATCTTATGACTTTT
TAAACAGATAACTAAAATTACAAACAAATCGTTTAACTTCAGGAGAGA
TTACATGAACAAAAATATAAATATCTCAAACTTTTTAACGAGTGAAAA
AGTACTCAACCAAATAATAAAACAATTGAATTTAAAAGAAACCGATAC
CGTTTACGAAATTGGAACAGGTAAAGGGCATTTAACGACGAAACTGGC
TAAAATAAGTAAACAGGTAACGTCTATTGAATTAGACAGTCATCTATT
CAACTTATCGTCAGAAAAATTAAAACTGAATACTCGTGTCACTTTAAT
TCACCAAGATATTCTACAGTTTCAATTCCCTAACAAACAGAGGTATAA
AATTGTTGGGAATATTCCTTACAATTTAAGCACACAAATTATTAAAAA
AGTGGTTTTTGAAAGCCGTGCGTCTGACATCTATCTGACTGTTGAAGA
AGGATTCTACAAGCGTACCTTGGATATTCACCGAACACTAGGGTTGCT
CTTGCACACTCAAGTCTCGATTCAGCAATTGCTTAAGCTGCCAGCGGA
ATGCTTTCATCCTAAACCAAAAGTAAACAGTGTCTTAATAAAACTTAC
CCGCCATACCACAGATGTTCCAGATAAATATTGGAAGCTATATAAGTA
CTTTGTTTCAAAATGGGTCAATCGAGAATATCGTCAACTGTTTACTAA
AAATCAGTTTCGTCAAGCAATGAAACACGCCAAAGTAAACAATTTAAG
TACCATTACTTATGAGCAAGTATTGTCTATTTTTAATAGTTATCTATT
ATTTAACGGAGGAAATAATTCTATGAGTCGCTTTTTTAAATTTGGAA
AGTTACACGTTACTAAAGGGAATGGAGACCGGGTCGACCCTTCAATA
GAGTTCTTAACGTTAATCCGAAAAAAACTAACGTTAATATTAAAAAAT
AAGATCCGCTTGTGAATTATGTATAATTTGATTAGACTAAAGAATAGG
AGAAAGTATGATGATATTTAAAAAACTTTCTCGTTAAGATAGGTTGTT
GGTGAGCATGTTATATACGGATGTATCGGTTTCCTTAATGCAAAATTT
TGTTGCTATCTTATTAATTTTTCTATTATATAGATATATTCAAAGAAA
GATAACATTTAAACGGATCATATTAGATATTTTAATAGCGATTATTTT
TTCAATATTATATCTGTTTATTTCAGATGCGTCATTACTTGTAATGGT
ATTAATGCGATTAGGGTGGCATTTTCATCAACAAAAAGAAAATAAGAT
AAAAACGACTGATACAGCTAATTTAATTCTAATTATCGTGATCCAGTT
ATTGTTAGTTGCGGTTGGGACTATTATTAGTCAGTTTACCATATCGAT
TATCAAAAGTGATTTCAGCCAAAATATATTGAACAATAGTGCAACAGA
TATAACTTTATTAGGTATTTTCTTTGCTGTTTTATTTGACGGCTTGTT
CTTTATATTATTGAAGAATAAGCGGACTGAATTACAACATTTAAATCA
AGAAATCATTGAATTTTCGTTAGAAAAACAATATTTTATATTTATATT
TATTTTATTTATAGTAATAGAAATTATTTTAGCAGTTGGGAATCTTCA

-continued

AGGAGTAACAGCCACGATATTATTAACCATTATCATTATTTTTTGTGT
CCTTATCGGGATGACTTTTTGGCAAGTGATGCTTTTTTTGAAGGCTTA
TTCGATTCGCCAAGAAGCCAATGACCAATTGGTCCGGAATCAACAACT
TCAAGATTATCTAGTCAATATCGAACAGCAGTACACCGAATTACGGCG
ATTTAAGCATGATTATCAAAACATCTTATTATCGTTGGAGAGTTTTGC
CGAAAAGGGCGATCAGCAACAGTTTAAGGCGTATTACCAAGAATTATT
AGCACAACGGCCAATTCAAAGTGAAATCCAAGGGGCAGTCATTGCACA
ACTCGACTACTTGAAAAATGATCCTATTCGAGGATTAGTCATTCAAAA
GTTTTTGGCAGCCAAACAGGCTGGTGTTACTTTAAAATTCGAAATGAC
CGAACCAATCGAATTAGCAACCGCTAATCTATTAACGGTTATTCGGAT
TATCGGTATTTTATTAGACAATGCGATTGAACAAGCCGTTCAAGAAAC
CGATCAATTGGTGAGTTGTGCTTTCTTACAATCTGATGGTTTAATCGA
AATTACGATTGAAAATACGGCCAGTCAAGTTAAGAATCTCCAAGCATT
TTCAGAGTTAGGCTATTCAACGAAAGGCGCTGGTCGGGGGACTGGTTT
AGCTAATGTGCAGGATTTGATTGCCAAACAAACCAATTTATTCTTAGA
AACACAGATTGAAAATAGAAAGTTACGACAGACATTGATGATTACGGA
GGAAACTTAATTTGTATCCCGTTTATTTATTAGAGGATGATTTACAGC
AACAAGCGATTTATCAGCAAATTATCGCGAATACGATTATGATTAACG
AATTTGCAATGACTTTAACATGCGCTGCCAGTGATACTGAGACATTGT
TGGCGGCAATTAAGGATCAGCAACGAGGTTTATTCTTTTTGGATATGG
AAATTGAGGATAACCGCCAAGCCGGTTTAGAAGTGGCAACTAAGATTC
GGCAGATGATGCCGTTTGCGCAAATTGTCTTCATTACAACCCACGAGG
AACTGACATTATTAACGTTAGAACGAAAAATAGCGCCTTTAGATTACA
TTCTCAAGGACCAAACAATGGCTGAAATCAAAAGGCAATTGATTGATG
ATCTATTGTTAGCTGAGAAGCAAAACGAGGCGGCAGCGTATCACCGAG
AAAATTTATTTAGTTATAAAATAGGTCCTCGCTTTTTCTCATTACCAT
TAAAGGAAGTTGTTTATTTATATACTGAAAAAGAAAATCCGGGTCATA
TTAATTTGTTAGCCGTTACCAGAAAGGTTACTTTTCCAGGAAATTTAA
ATGCGCTGGAAGCCCAATATCCAATGCTCTTTCGGTGTGATAAAAGTT
ACTTAGTTAACCTATCTAATATTGCCAATTATGACAGTAAAACACGGA
GTTTAAAATTTGTAGATGGCAGTGAGGCAAAAGTCTCGTTCCGGAAAT
CACGGGAACTAGTGGCCAAATTAAAACAAATGATGTAGCGCCTGCAGG
CACGCCAAATGATCCCAGTAAAAAGCCACCCGCATGGCGGGTGGCTTT
TTATTAGCCCTAGAAGGGCTTCCCACACGCATTTCAGCGCCTTAGTGC
CTTAGTTTGTGAATCATAGGTGGTATAGTCCCGAAATACCCGTCTAAG
GAATTGTCAGATAGGCCTAATGACTGGCTTTTATAATATGAGATAATG
CCGACTGTACTTTTTACAGTCGGTTTTCTAATGTCACTAACCTGCCCC
GTTAGTTGAAGAAGGTTTTTATATTACAGCTCCAGATCTACCGGTTTA
ATTTGAAAATTGATATTAGCGTTTAACAGTTAAATTAATACGTTAATA
ATTTTTTTGTCTTTAAATAGGGATTTGAAGCATAATGGTGTTATAGCG

```
                                          -continued
TACTTAGCTGGCCAGCATATATGTATTCTATAAAATACTATTACTACC

AAGAATAACTTTCATCGTAAAAGGCAAGTAATTGAGGAAACTTGAAGT

TTTTCTCTATTACTTGCCTTCTTTATTTTATTAAGCTAAATATGTTTT

AAATAATTAACTATAACGGACCTGCTTGGCGGAAACTAAACAGTAAGA

ACTTTAAATTATAAAAATCTGCAACCGTTTTCTAAAATTTTGCGCAAG

CGGTTGCGCAAAATTTTTAAATTTGATATTATTAATATTGCAATAATT

CATGAAGCGCTTACAATAATCACAAGTGTCTTTTAGAACTATTTTATA

AGTTAAGGAGTTGTTAGCAATGCAAACAATGCACTTCTTACTTGCAAT

GGCTCCACCCCCGTATCATCAACAGTATTTTCAGCATTTTCAAGGAAT

GGAAGATAACTGGATAATATGGCTTTTCGTGTGGGTAATTATCATTGA

CATAATAACAGGGACGGCAAGGAGTTTAGTAACGCATCATACAACATC

AACTAAAGGCACATCAGGCTTAATCAAGCATGGCATCCTATTAATAAT

AATCCTGACGCTTTATCCAATGCTTGATATTAATGGTATGAAAAGCGC

CGGCGATACCTTTACGATGTTTTATGTATTATTCTATGCTGTTTCAAT

AATTGAGAATTGCGGACAAA
```

In SEQ ID NO:2 shown above, underline indicates an exemplary terminator sequence, italics indicates an exemplary erythromycin resistant marker, bold underline indicates an exemplary maltose inducible promoter coding sequence, and bold indicates an exemplary holin coding sequence. For generating a stable plasmid in an antibiotic-independent manner, the erythromycin resistant marker can be replaced with the thyA gene, as discussed elsewhere herein. For producing biologics other than holin, the holin coding sequence can be replaced with a coding sequence of a different biologic or a gene product responsible for producing a different biologic.

The microorganism can be engineered using any methods known in the art. General methods are provided in Green et al. 2012. Methods for engineering lactic acid bacteria such as *L. lactis* are provided by van Pijkeren and Britton et al. 2012, van Pijkeren and Neoh et al. 2012, Oh et al. 2014, and Barrangou et al. 2016.

In some versions of the invention, one or more of the biologics are produced by the microorganism and secreted from the microorganism in a maltose-dependent manner without the need for lysis. In the case of polypeptide biologics, for example, the microorganism may comprise a recombinant gene configured to express and secrete the polypeptide. Elements for engineering a microorganism to secrete a polypeptide are well known in the art. Typical elements include a signal peptide-encoding sequence placed upstream of—and in-frame with—the coding sequence of the polypeptide to be secreted. The sequences of a large number of signal peptides for bacteria are known in the art. Exemplary signal peptide sequences are available at http://www.cbs.dtu.dk/services/SignalP/. The signal peptide may be cleaved from or remain intact on the polypeptide after secretion.

In certain versions of the invention, the microorganism is administered to a subject in a manner that introduces one or more biologics to the gastrointestinal tract. This can be accomplished at least in part due to the maltose-inducible promoter. Portions of the gastrointestinal tract, such as the small intestine, have relatively high levels of maltose, particularly after the consumption of starch. A microorganism of the invention configured to release a biologic in a maltose-dependent manner can be administered to the gastrointestinal tract, wherein the microorganism will release the biologic in the gastrointestinal tract after exposure to the maltose. If the microorganism is configured to express and directly secrete the biologic in a maltose-dependent manner, the microorganism will secrete the biologic after exposure to the maltose. If the microorganism is configured to express a lytic protein and release a non-secreted biologic, the microorganism will lyse and release the non-secreted biologic after exposure to the maltose.

The microorganism can be administered to the gastrointestinal tract by any method known in the art. The microorganism may be administered orally, rectally, or directly into the gastrointestinal tract via a stoma. The microorganism is preferably administered directly into or upstream of the small intestines, so that the microorganism ultimately passes through or into the small intestines. The bacterium may be swallowed or introduced via a tube.

The bacterium may be combined in a composition with a pharmaceutically acceptable excipient, carrier, buffer, stabilizer or other material well known to those skilled in the art. Such materials should be non-toxic and should not interfere with the efficacy of the bacterium. The precise nature of the carrier or other material may depend on the route of administration. The composition may be liquid, solid, or semi-solid. The composition may comprise a foodstuff or may take the form of a pharmaceutical composition. Those of relevant skill in the art are well able to prepare suitable compositions.

The subject to which the bacterium is administered may be an animal, such as a mammal or, more specifically, a human.

To ensure there is a sufficient amount of maltose in the gastrointestinal tract to induce release of the biologic therein, maltose or a maltose precursor can be administered to the gastrointestinal tract of the subject before, during, or after administering the microorganism. Any carbohydrate that can be degraded to maltose can serve as a suitable maltose precursor. In some cases, the carbohydrate is degraded to maltose by natural enzymes produced by the subject. In some cases, the carbohydrate is degraded to maltose by enzymes co-administered to the subject along with the maltose precursor. An exemplary maltose precursor is starch. An exemplary enzyme that degrades starch to maltose is amylase (salivary and pancreatic forms). The maltose or maltose precursor (and, optionally, any enzyme responsible for degrading the maltose precursor to maltose) can be administered within (before or after) 5 hours, 4 hours, 3 hours, 2 hours, 1 hour or less of administering the microorganism. The maltose or maltose precursor (and, optionally, any enzyme responsible for degrading the maltose precursor to maltose) is preferably administered in an amount sufficient to stimulate or increase release of the biologic in the subject. The maltose or maltose precursor (and, optionally, any enzyme responsible for degrading the maltose precursor to maltose) may all be administered in the same composition or may be administered in separate compositions.

The administered starch may be substantially purified starch. "Substantially purified starch" refers to processed compositions that contain starch in an amount of at least about 50% w/w, at least about 55% w/w, at least about 60% w/w, at least about 65% w/w, at least about 70% w/w, at least about 75% w/w, at least about 80% w/w, at least about 85% w/w, at least about 90% w/w, or at least about 95% w/w.

In certain versions of the invention, the microorganism is used to produce a biologic in vitro. The microorganism may be cultured in the presence of a sufficient amount of maltose to induce production and/or release of the biologic from the microorganism. The maltose may be provided in the form of maltose or a maltose precursor, either with or without carbohydrate-degrading enzymes. Alternatively or additionally, the microorganism may be primed in a maltose-containing medium and then subsequently cultured in a low-maltose or no-maltose medium. The microorganism may be cultured in a reactor or other suitable site for producing the biologic.

Due to the lag period associated with gene transcription, the microorganism can be "primed" with maltose at a first time period such that the microorganism releases the biologic at a second time period. This method can be used, for example, for releasing the biologic at sites in the body that do not contain maltose or contain maltose only in low concentrations. This method can alternatively be used for releasing the biologic at in vitro sites that do not contain maltose or contain maltose only in low concentrations. The priming can be performed by contacting the microorganism with a maltose-containing medium prior to administering the microorganism to the subject. The maltose-containing medium preferably comprises an amount of maltose sufficient to induce expression of the gene product, and the contacting is preferably conducted for a time sufficient to induce expression of the gene product. The amount of maltose sufficient to induce expression of the gene product in some cases is a relative amount of maltose with respect to sugars or other factors that may repress expression of the gene product. The contacting is preferably conducted in vitro. The contacting is preferably performed for a time period of from about 10 minutes to about 80 minutes, such as about 20 minutes to about 70 minutes, about 30 minutes to about 60 minutes, about 40 minutes to about 50 minutes, or about 45 minutes. The microorganism is preferably administered to the subject within 60 about minutes, within about 50 minutes, within about 40 minutes, within about 30 minutes, within about 20 minutes, within about 10 minutes, within about 10 minutes, within about 5 minutes, or within about 3 minutes of completing the priming. The microorganism can be administered to the gastrointestinal tract of the subject for release of the biologic therein or to other sites of the subject's body for release of the biologic therein.

In some versions of the invention, the microorganisms can be configured to enter cells of the subject and release the biologic within the cells of the subject. This can be accomplished by engineering the microorganism to express internalin A (InlA).

The maltose-inducible promoter described herein can also be used for genetic engineering purposes. Efficient genome engineering is key to further improve industrial strains, to engineer probiotics as delivery vehicles, and to understand biological (probiotic) function. The approach of Campbell-like homologous recombination is widely used for genetic engineering purposes, especially for gene insertions and deletions. A commonly used application to modify genomes of lactic acid bacteria is by the application of a temperature-sensitive helper plasmid (that provides RepA in trans) combined with a repA-vector that contains DNA sequences homologous to target locations in the chromosome. Once both vectors are established in the cell, the helper plasmid is cured following growth at increased temperatures, after which the repA-vector is integrated in the chromosome (single-cross over). The latter is typically easily to identify by means of antibiotic selection encoded from the repA-backbone.

There are several shortcomings of the conventional Campbell-like system, however. First, the applicability of high temperatures is unfavorable because it induces increased stress. This increased stress may yield an increase in undesired mutations in the genome, especially when taking into consideration that prolonged culturing of the bacteria at high temperatures is required to cure the helper-plasmid. Second, the process can take up to one week, after which only approximately 50% of the population is cured from the helper plasmid.

Figure 6:
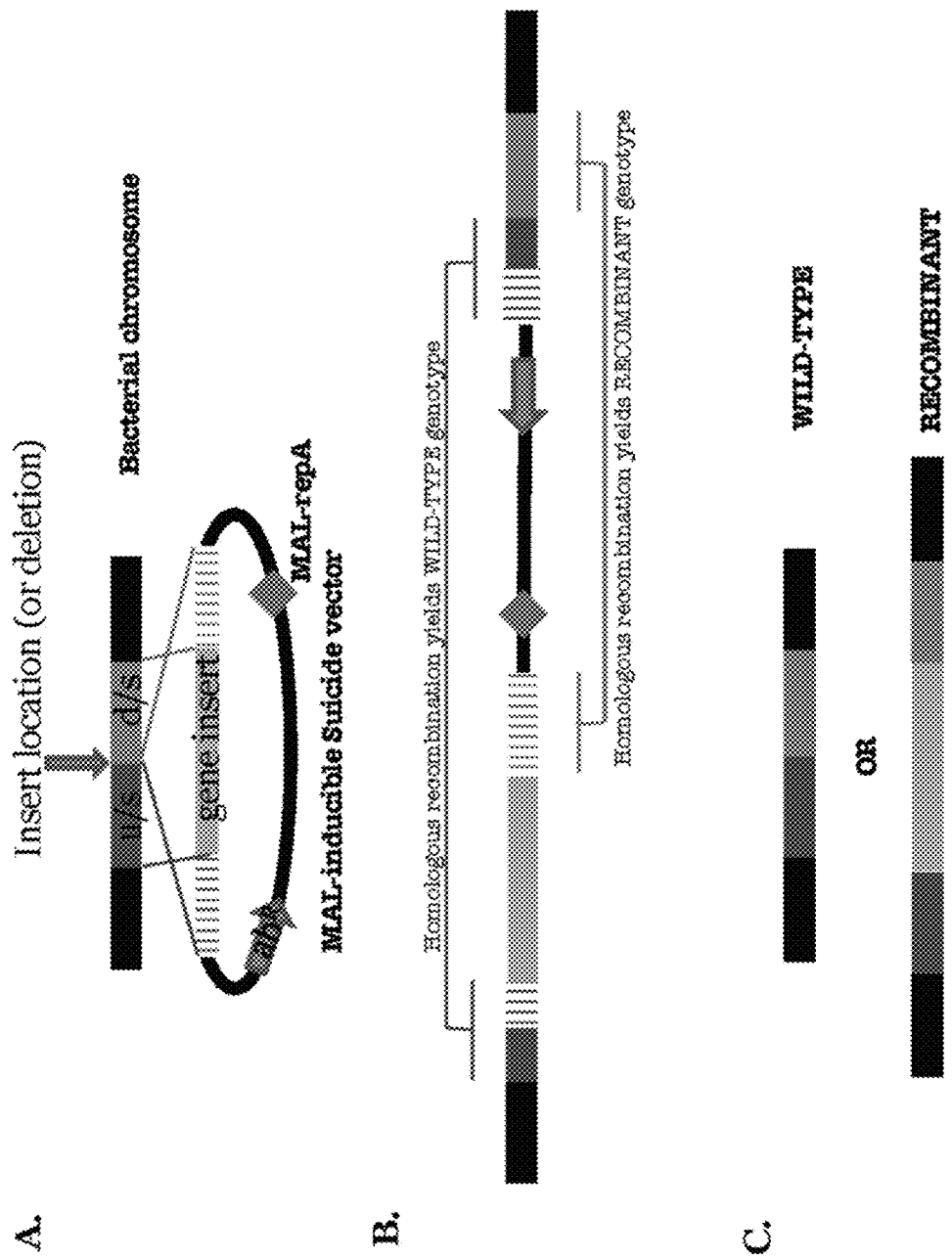
FIG. 6 shows a schema of a method of genetic engineering using a maltose-inducible promoter combined with repA.

The maltose-inducible promoter combined with repA alleviates all of the above concerns, omitting the need to use the temperature sensitive plasmid. On a previously repA-vector, the maltose promoter fused to repA is cloned. Upon transformation of the bacteria in the presence of maltose, RepA is produced which allows temporarily replication. Transformants (>2,000) are routinely observed in the presence of maltose. However, when the cells are plated on glucose the colony numbers dramatically reduce. This approach allows specific selection for replication, which can be expanded to select for single cross-over. The selection can happen overnight. A schema of this process is shown in FIG. 6.

The elements and method steps described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

It is understood that the invention is not confined to the particular construction and arrangement of parts herein illustrated and described, but embraces such modified forms thereof as come within the scope of the claims.

EXAMPLES

Microorganisms as Biologic Delivery Vehicles

FIG. 1 shows a schema for an exemplary microorganism of the invention modified for use as a biologic delivery vehicle. The biologic shown in FIG. 1 is a bacteriophage produced by a modified L. reuteri microorganism. DNA of a pathogen-derived bacteriophage is fused with a plasmid origin of replication (ORI), a L. reuteri auxotrophic marker (thyA), and a CRISPR (Clustered, Regularly Interspaced Short Palindromic Repeats)-cassette to generate a phasmid. The phasmid-encoded auxotrophic marker, when deleted on the L. reuteri chromosome, yields stable phasmid replication in L. reuteri. The phasmid will produce in L. reuteri virions that encode engineered CRISPR arrays. The CRISPR arrays can be designed to target pathogens in a strain-specific manner. Expression of internalin A (InlA) can localize *L. reuteri* intracellularly for subsequent virion release. For extracellular delivery (i.e., in the lumen of the gastrointestinal tract, etc.), InlA is not required. The microorganism can be engineered to lyse and deliver the biologic after ingestion by harboring a lytic protein gene (holin and/or lysin) operably connected to a promoter that is specifically activated in the presence of maltose, a disaccharide sugar that is abundant in the small intestine of mammals. This leads to expression of the lytic protein (holin and/or lysin), lysis of the microorganism, and delivery of the biologic to its intended destination. In addition to virion delivery, complete lysis is also a robust approach to achieve biological containment.

The schema outlined in FIG. 1 can be used for microorganisms other than *L. reuteri* and biologics other than bacteriophages. For example, a microorganism can stably harbor a maltose-inducible gene encoding a protein biologic (e.g., an antibody, antibiotic, enzyme, etc.) or a protein responsible for making a biologic. Maltose-induced lysis of the microorganism will then release the protein biologic from the microorganism.

Lactobacillus reuteri as an Exemplary Biologic Delivery Platform

*L. reuteri* is a microorganism amenable to genetic manipulation (van Pijkeren et al. 2009, Oh et al. 2014, van Pijkeren and Britton et al. 2012, van Pijkeren and Neoh et al. 2012, van Pijkeren et al, 2014), is capable of surviving passage through human and murine gastrointestinal tracts (Frese et al. 2010, Oh et al. 2010), and exhibits probiotic features, such as anti-inflammatory properties (Thomas et al. 2012, Liu et al. 2010), prevention of bone loss (Britton et al 2014), and amelioration of infection by pathogenic *E. coli* (Eaton et al. 2011). These characteristics make *L. reuteri* a suitable exemplary microorganism for use as a platform for delivering biologics to the gastrointestinal tract. The particular *L. reuteri* strain used in the present examples (VPL1014) is an undomesticated strain directly derived from *L. reuteri* ATCC PTA 6475.

Antibiotic-Independent Plasmid Stability

In-trans expression of thyA in *L. reuteri* ΔthyA stably maintains extra-chromosomal DNA in the cell. Native thyA was inactivated by single-stranded DNA recombineering (van Pijkeren and Britton et al. 2012, van Pijkeren and Neoh et al. 2012) to yield *L. reuteri* ΔthyA, which makes the cells dependent on exogenously added thymidine in minimal medium. To demonstrate that *L. reuteri* ΔthyA can be used as a host to stably maintain extra-chromosomal elements that encode ThyA, we cloned thyA with its native promoter in the backbone of pSIP411 (Em$^R$), yielding pSIP-thyA. *L. reuteri* ΔthyA harboring pSIP-thyA and *L. reuteri* wild-type harboring pSIP411 were cultured in minimal medium lacking thymidine in the absence of antibiotic. Stability of pSIP411 and pSIP-thyA was determined by the ratio of total number of cells and Em$^R$ cells. After 50 generations only 20±0.9% of *L. reuteri* wild-type retained pSIP411, while 96±5% of *L. reuteri* ΔthyA retained pSIP-thyA. These data show an approach to maintain unstable plasmids in *L. reuteri*.

Induced Lysis for Biologic Delivery and Biological Containment

Lysis is an efficient way to release biologics in situ, and complete lysis achieves biological containment. Native lysin expression can result in lysis of the expression host, as previously demonstrated in *L. lactis* (de Ruyter et al. 1997).

The phage search tool (PHAST) (Zhou et al. 2011) revealed the presence of 4 prophages in *L. reuteri* of which 2 are predicted to be intact, all encoding holin-lysin gene clusters. Induced expression of holins alone do induce lysis (de Ruyter et al. 1997, Shi et al. 2012) as a consequence of increased membrane permeability, possibly combined with the presence of native endonucleases.

Figure 2:
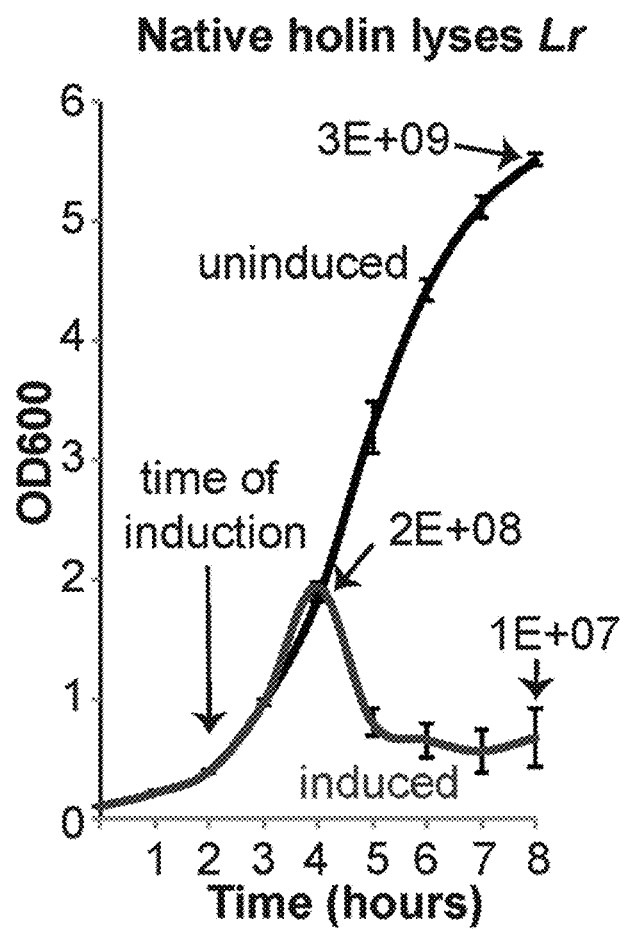
FIG. 2 shows lysis of *L. reuteri* mediated by holin expressed from an inducible promoter as an exemplary lytic protein gene. Data shown are averages of three experiments, and error bars indicate standard deviation. Average viability levels are indicated.

We cloned a bacteriophage-derived holin gene in the inducible expression vector pSIP57, and confirmed induced lysis in *L. reuteri* (FIG. 2). *L. reuteri* cells harboring pSIP-holin were cultured overnight and diluted to OD600=0.1. At OD600=1 the culture was split, and one culture was induced for holin expression. Expression of the holin lysed *L. reuteri* killing 95% of the population.

These data confirm that we can induce lysis in *L. reuteri*, which we can further optimize and exploit for efficient local biologic release.

Maltose-Dependent Lysis

Figure 4:
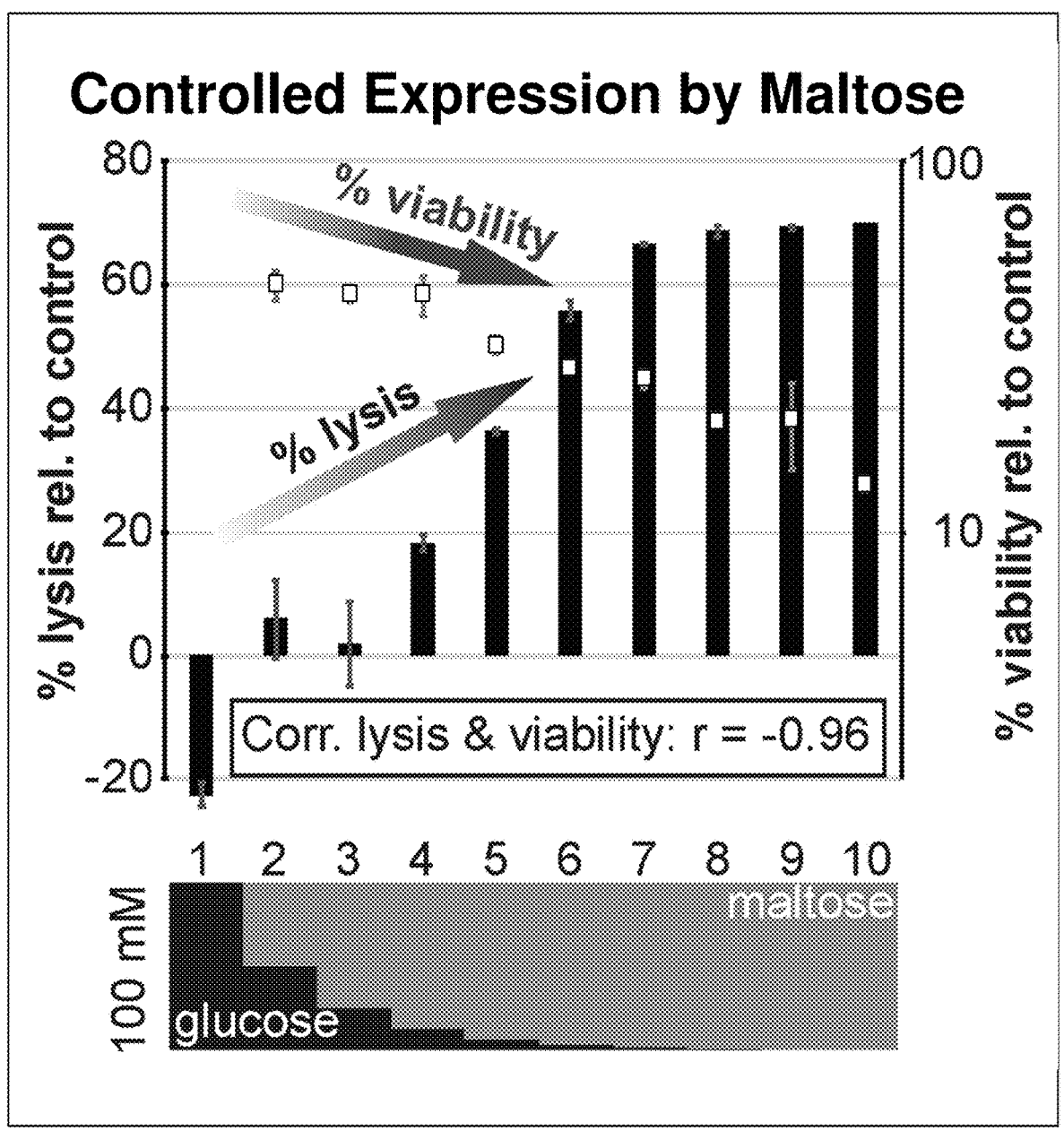
FIG. 4 shows percent lysis relative to control (black bars) and % viability relative to control (white boxes) for *L. reuteri* harboring the maltose-inducible holin gene in pVPL3628 in the presence of various relative amounts of glucose and maltose at 100 mM total sugar. Data shown are averages of two independent experiments. Error bars indicate standard deviation.

Controlling microorganism lysis can aid with delivery of biologics to various regions in the body, such as the gastrointestinal tract. We identified a promoter in *L. reuteri* that is activated upon sensing maltose, a disaccharide present in the small intestine of mice and humans (Tannock et al. 2011, Fogel et al. 1973). We fused the maltose-inducible promoter to the *L. reuteri* holin gene, and we confirmed lysis of cells when grown in the presence of maltose alone or in a mixture of different ratios of maltose and glucose (FIG. 4).

*L. reuteri* harboring pSIP411 (control) or a pSIP411-derived plasmid containing the holin gene under the control of a maltose-inducible promoter (pVPL3628; FIG. 3; SEQ ID NO:2), was cultured in modified MRS (mMRS) with glucose as a sole carbon source to OD600=0.4. Cells were washed twice in PBS, and resuspended in mMRS containing 100 mM sugar, which was either glucose only (bar #1), maltose only (bar #10) or different ratios of glucose-to-maltose (bars #2-9), i.e. 50-50, 25-75, 12.5-87.5, etc, as indicated in the bottom panel of FIG. 4. After two hours growth, the reduction in OD600 of *L. reuteri* expressing the holin was expressed relative to that of the control as % lysis (primary axis). In analogy, on the secondary axis is the reduction in viability plotted. With a 50-50 mix of glucose and maltose, a 50% reduction of viability was observed for *L. reuteri* expressing the holin.

When *L. reuteri* was cultured in medium containing maltose and equimolar levels of lactose, or fructose, or galactose, or an equimolar mix of these three sugars, the activity of the maltose-inducible promoter was similar to cells cultured in medium containing maltose only (data not shown).

These data demonstrate robust maltose-dependent transcriptional activation. Since *L. reuteri* utilizes mainly non-complex sugars for growth, the present system allows for induced lysis of *L. reuteri* once it reaches the small intestine, which is expected to yield in-situ biologic delivery.

Maltose Priming of *L. reuteri*

Figure 5:
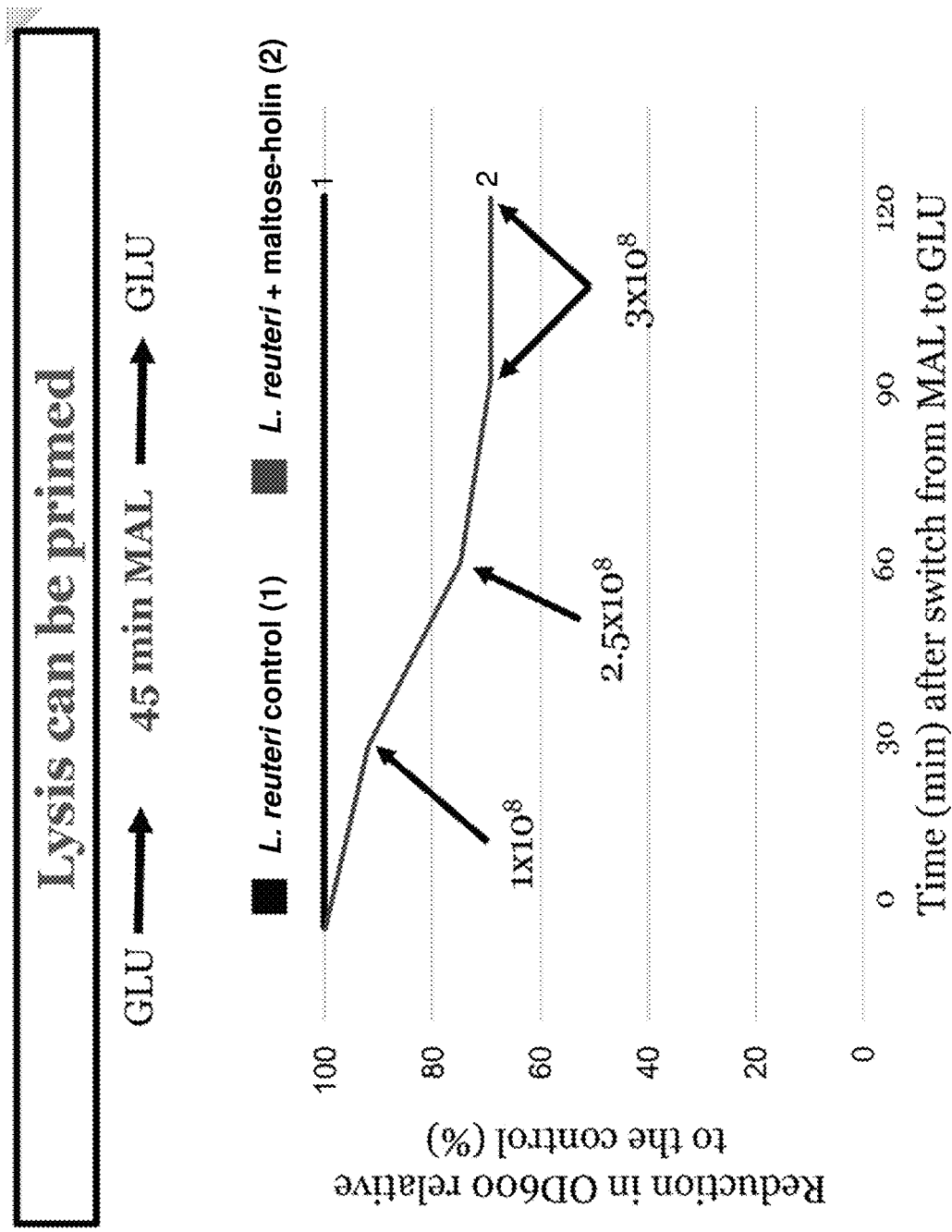
FIG. 5 shows OD600 of *L. reuteri* harboring the maltose-inducible holin gene in pVPL3628 (*L. reuteri*+maltose-holin) relative to *L. reuteri* harboring an equivalent plasmid but lacking the maltose-inducible holin gene (*L. reuteri* control) in glucose (GLU) after exposure for 45 minutes in maltose (MAL).

*L. reuteri* harboring the maltose-inducible holin gene can be primed with maltose to control the timing of lysis after administration. *L. reuteri* harboring pSIP411 (control) or a pSIP411-derived plasmid containing the holin gene under the control of a maltose-inducible promoter (pVPL3628; FIG. 3; SEQ ID NO:2) was cultured in modified MRS (mMRS) with glucose as a sole carbon source to OD600=0.4. Cells were washed twice in PBS, resuspended in mMRS containing 100 mM maltose, and cultured for 45 minutes. After 45 minutes of growth, the cells were transferred to mMRS containing glucose as the sole carbon source, and the OD600 of *L. reuteri* expressing the holin was determined relative to that of the control. As shown in FIG. 5, prior priming of *L. reuteri* harboring the maltose-inducible holin gene in maltose induced lysis even after transfer to glucose-only medium. These data show that priming *L. reuteri* with maltose can be employed for delivering biologics to areas of the body in a manner independent of the maltose concentration at such areas of the body.

Intracellular Biologic Delivery

*L. reuteri* can be engineered to deliver biologics intracellularly. This can be accomplished by engineering *L. reuteri* to internalize in cells, preferably prior to lysis. Intracellular trafficking and replication of (facultative) anaerobe bacteria are well-established phenomena (Sznol et al. 2000, Cronin et al. 2012, Pálffy et al. 2006). Intracellular entry of *L. reuteri* can be achieved by expression of the *L. monocytogenes* internalin A (InlA) protein, as previously has been shown in *L. lactis* (Guimarães et al. 2005). InlA complexes with E-cadherin and mediates the invasion of LMO in mammalian cells (Lecuit et al. 1997), including in solid breast tumor cells (van Pijkeren et al. 2010). Colorectal cancer (CRC) cells are also of epithelial origin and express E-cadherin (Elzagheid et al. 2006), which allows InlA-mediated invasion. To engineer *L. reuteri* to enter cells, inlA can be codon-optimized for expression in *L. reuteri* and placed under the control of a constitutive promoter, such as $P_{HELP}$ (Riedel et al. 2007).

EXEMPLARY VERSIONS OF THE INVENTION

Exemplary versions of the invention are as follows:

Version 1a. A microorganism harboring a recombinant gene, wherein the recombinant gene comprises a maltose-inducible promoter operably connected to a coding sequence of a first biologic.

Version 2a. The microorganism of version 1a, wherein the maltose-inducible promoter comprises a sequence at least about 80% identical to SEQ ID NO:1.

Version 3a. The microorganism of any one of versions 1a-2a, wherein expression of the first biologic from the coding sequence effects release of the first biologic from the microorganism.

Version 4a. The microorganism of any one of versions 1a-3a, wherein the first biologic comprises a lytic protein.

Version 5a. The microorganism of any one of versions 1a-4a, wherein the first biologic comprises a lytic protein selected from the group consisting of a holin and a lysin.

Version 6a. The microorganism of any one of versions 1a-5a, wherein the first biologic effects lysis of the microorganism.

Version 7a. The microorganism of any one of versions 1a-6a, wherein the first biologic effects release of a second biologic made by the microorganism.

Version 8a. The microorganism of version 7a, wherein the second biologic is selected from the group consisting of a carbohydrate, a polypeptide, a nucleic acid, a metabolite, a virus and a combination thereof.

Version 9a. The microorganism of any one of versions 7a-8a, wherein the microorganism is genetically modified to enhance production of the second biologic.

Version 10a. The microorganism of any one of versions 7a-9a, wherein the second biologic is a polypeptide produced from a recombinant gene.

Version 11a. The microorganism of any one of versions 1a-3a, wherein the first biologic comprises a biologic that is secreted from the microorganism without lysis of the microorganism.

Version 12a. The microorganism of version 11a, wherein the first biologic comprises a polypeptide comprising a signal sequence.

Version 13a. The microorganism of version 1a, wherein the first biologic comprises an RNA.

Version 14a. The microorganism of version 13a, wherein the RNA is an antisense RNA.

Version 15a. The microorganism of any one of versions 1a-14a, wherein the microorganism comprises a bacterium.

Version 16a. The microorganism of any one of versions 1a-15a, wherein the microorganism comprises a member of lactic acid bacteria.

Version 17a. The microorganism of any one of versions 1a-16a, wherein the microorganism comprises a member of *Lactobacillus*.

Version 18a. The microorganism of any one of versions 1a-17a, wherein the microorganism comprises *Lactobacillus reuteri*.

Version 19a. The microorganism of any one of versions 1a-18a, wherein the microorganism comprises a bacterium other than *Lactobacillus reuteri* 100-23.

Version 1b. A method of producing a biologic, the method comprising exposing a microorganism as recited in any one of versions 1a-19a to an amount of maltose sufficient to stimulate production of the first biologic from the coding sequence.

Version 2b. The method of version 1b, wherein the biologic is an RNA.

Version 3c. The method of version 2b, wherein the RNA is an antisense RNA and production of the antisense RNA reduces expression of a gene comprising a sequence complementary to a sequence of the antisense RNA.

Version 1c. A method of introducing a biologic to a site, the method comprising introducing a microorganism harboring a recombinant gene to the site, wherein the recombinant gene comprises a maltose-inducible promoter operably connected to a coding sequence of a first biologic, wherein expression of the first biologic from the coding sequence effects release of the first biologic from the microorganism at the site.

Version 2c. The method of version 1c, wherein the maltose-inducible promoter comprises a sequence at least about 80% identical to SEQ ID NO:1.

Version 3c. The method of any one of versions 1c-2c, wherein the first biologic comprises a lytic protein.

Version 4c. The method of any one of versions 1c-3c, wherein the first biologic comprises a lytic protein selected from the group consisting of a holin and a lysin. Version 5c. The method of any one of versions 1c-4c, wherein the first biologic effects lysis of the microorganism at the site.

Version 6c. The method of any one of versions 1c-5c, wherein the first biologic effects release of a second biologic made by the microorganism at the site.

Version 7c. The method of version 6c, wherein the second biologic is selected from the group consisting of a carbohydrate, a polypeptide, a nucleic acid, a metabolite, and a combination thereof.

Version 8c. The method of any one of versions 6c-7c, wherein the microorganism is genetically modified to enhance production of the second biologic.

Version 9c. The method of any one of versions 6c-8c, wherein the second biologic is a polypeptide produced from a recombinant gene.

Version 10c. The method of any one of versions 1c-2c, wherein the first biologic comprises a biologic that is secreted from the microorganism without lysis of the microorganism.

Version 11c. The method of version 10c, wherein the first biologic comprises a polypeptide comprising a signal sequence.

Version 12c. The method of any one of versions 1c-11c, wherein the microorganism comprises a bacterium.

Version 13c. The method of any one of versions 1c-12c, wherein the microorganism comprises a member of lactic acid bacteria.

Version 14c. The method of any one of versions 1c-13c, wherein the microorganism comprises a member of *Lactobacillus*.

Version 15c. The method of any one of versions 1c-14c, wherein the microorganism comprises *Lactobacillus reuteri*.

Version 16c. The method of any one of versions 1c-15c, wherein the microorganism comprises a bacterium other than *Lactobacillus reuteri* 100-23.

Version 17c. The method of any one of versions 1c-16c, wherein the introducing the microorganism comprises introducing the microorganism to an in vitro site.

Version 18c. The method of version 17c, wherein the in vitro site comprises an amount of maltose sufficient to induce expression of the gene product.

Version 19c. The method of any one of versions 1c-16c, wherein the introducing the microorganism comprises introducing the microorganism to an in vivo site in a subject.

Version 20c. The method of any one of versions 1c-16c and 19c, wherein the site is a gastrointestinal tract of a subject.

Version 21c. The method of any one of versions 19c-20c, wherein the introducing the microorganism comprises orally administering the microorganism to a subject.

Version 22c. The method of any one of versions 19c-21c, wherein the subject is a mammal.

Version 23c. The method of any one of versions 19c-22c, wherein the subject is a human.

Version 24c. The method of any one of versions 1c-23c, further comprising introducing maltose or a maltose precursor to the site before, during, or after the introducing the microorganism to the site.

Version 25c. The method of version 24c wherein the maltose precursor comprises starch.

Version 26c. The method of any one of versions 1c-25c, further comprising, prior to the introducing the microorganism to the site, contacting the microorganism with a maltose-containing medium.

Version 27c. The method of version 26c, wherein the maltose-containing medium comprises an amount of maltose sufficient to induce expression of the gene product and wherein the contacting is conducted for a time sufficient to induce expression of the gene product.

Version 28c. The method of any one of versions 26c-27c, wherein the contacting is conducted in vitro.

The invention encompasses any combination of the above versions, whether explicitly stated or not.

CITED REFERENCES

Alvarez-Sieiro P, Montalbán-López M, Mu D, Kuipers O P. Bacteriocins of lactic acid bacteria: extending the family. *Appl Microbiol Biotechnol*. 2016. 100(7):2939-51.

Bahey-El-Din M, Gahan C G M, Griffin B T. 2010. *Lactococcus lactis* as a cell factory for delivery of therapeutic proteins. *Curr Gene Ther* 10:34-45.

Barrangou R, van Pijkeren J P. Exploiting CRISPR-Cas immune systems for genome editing in bacteria. *Curr Opin Biotechnol*. 2016 February; 37:61-8.

Becker S C, Dong S, Baker J R, Foster-Frey J, Pritchard D G, Donovan D M. 2009. LysK CHAP endopeptidase domain is required for lysis of live staphylococcal cells. *FEMS Microbiol Lett* 294:52-60.

Beisel C L, Gomaa A A, Barrangou R. 2014. A CRISPR design for next-generation antimicrobials. *Genome Biol* 15:516.

Bikard D, Euler C W, Jiang W, Nussenzweig P M, Goldberg G W, Duportet X, Fischetti V A, Marraffini L A. 2014. Exploiting CRISPR-Cas nucleases to produce sequence-specific antimicrobials. *Nat Biotech* 32:1146-1150.

Borysowski J, Weber-Dabrowska B, Górski A. Bacteriophage endolysins as a novel class of antibacterial agents. *Exp Biol Med* (Maywood). 2006 April; 231(4):366-77.

Britton, R. A.; Irwin, R.; Quach, D.; Schaefer, L.; Zhang, J.; Lee, T.; Parameswaran, N.; McCabe, L. R. Probiotic *L. reuteri* Treatment Prevents Bone Loss in a Menopausal Ovariectomized Mouse Model. *J Cell Physiol* 2014, 229 (11), n/a-n/a DOI: 10.1002/jcp.24636.

Chatel J-M, Pothelune L, Ah-Leung S, Corthier G, Wal J-M, Langella P. 2008. In vivo transfer of plasmid from food-grade transiting lactococci to murine epithelial cells. Gene Ther 15:1184-1190.

Cheng X, Zhang X, Pflugrath J W, Studier F W. 1994. The structure of bacteriophage T7 lysozyme, a zinc amidase and an inhibitor of T7 RNA polymerase. Proc Natl Acad Sci USA 91:4034-4038.

Citorik R J, Mimee M, Lu T K. 2014. Sequence-specific antimicrobials using efficiently delivered RNA-guided nucleases. Nat Biotech 32:1141-1145.

Cotter P D, Ross R P, Hill C. 2013. Bacteriocins I[mdash]I a viable alternative to antibiotics? Nat Rev Microbiol 11:95-105.

Cronin, M.; Akin, A. R.; Collins, S. A.; Meganck, J.; Kim, J.-B.; Baban, C. K.; Joyce, S. A.; van Dam, G. M.; Zhang, N.; van Sinderen, D.; et al. High resolution in vivo bioluminescent imaging for the study of bacterial tumour targeting. *PLoS ONE* 2012, 7 (1), e30940 DOI:10.1371/journal.pone.0030940.

de Azevedo M, Karczewski J, Lefèvre F, Azevedo V, Miyoshi A, Wells J M, Langella P, Chatel J-M. 2012. In vitro and in vivo characterization of DNA delivery using recombinant *Lactococcus lactis* expressing a mutated form of *L. monocytogenes* Internalin A. BMC Microbiol 12:299.

de Ruyter, P. G.; Kuipers, O. P.; Meijer, W. C.; de Vos, W. M. Food-grade controlled lysis of *Lactococcus lactis* for accelerated cheese ripening. *Nat Biotech* 1997, 15 (10), 976-979 DOI:10.1038/nbt1097-976

De Weirdt R, Crabbé A, Roos S, Vollenweider S, Lacroix C, van Pijkeren J-P, Britton R A, Sarker S, Van de Wiele T, Nickerson C A. 2012. Glycerol Supplementation Enhances *L. reuteri*'s Protective Effect against *S. Typhimurium* Colonization in a 3-D Model of Colonic Epithelium. PLoS ONE 7:e37116.

Dishisha T, Pereyra L P, Pyo S-H, Britton R A, Hatti-Kaul R. 2014. Flux analysis of the *Lactobacillus reuteri* propanediol-utilization pathway for production of 3-hydroxypropionaldehyde, 3-hydroxypropionic acid and 1,3-propanediol from glycerol. Microb Cell Fact 13:76.

Doleyres Y, Beck P, Vollenweider S, Lacroix C. 2005. Production of 3-hydroxypropionaldehyde using a two-step process with *Lactobacillus reuteri*. Appl Microbiol Biotechnol 68:467-474.

Eaton, K. A.; Honkala, A.; Auchtung, T. A.; Britton, R. A. Probiotic *Lactobacillus reuteri* Ameliorates Disease Due to Enterohemorrhagic *Escherichia coli* in Germfree Mice. *Infect Immun* 2011, 79 (1), 185-191 DOI: 10.1128/IAI.00880-10.

Elzagheid, A.; Algars, A.; Bendardaf, R.; Lamlum, H.; Ristamaki, R.; Collan, Y.; Syrjanen, K.; Pyrhonen, S. E-cadherin expression pattern in primary colorectal carcinomas and their metastases reflects disease outcome. *World J Gastroenterol* 2006, 12 (27), 4304-4309.

Feliza A. Bourguet, Brian E. Souza, Angela K. Hinz, Matthew A. Coleman, and Paul J. Jackson. Characterization of a Novel Lytic Protein Encoded by the *Bacillus cereus* E33L Gene ampD as a *Bacillus anthracis* Antimicrobial Protein. *Appl Environ Microbiol.* 2012 April; 78(8): 3025-3027.

Field D, Connor P M O, Cotter P D, Hill C, Ross R P. 2008. The generation of nisin variants with enhanced activity against specific gram-positive pathogens.—PubMed—NCBI. Mol Microbiol 69:218-230.

Field D, Begley M, O'Connor P M, Daly K M, Hugenholtz F, Cotter P D, Hill C, Ross R P. 2012. Bioengineered Nisin A Derivatives with Enhanced Activity against Both Gram Positive and Gram Negative Pathogens. PLoS ONE 7:e46884

Fischetti V A. 2004. The use of phage lytic enzymes to control bacterial infections, p 321-334 In Kutter E, Sulakvelidze A, editors. (ed), Bacteriophages: biology and applications. CRC Press, Boca Raton, Fla.

Fischetti V A. 2009. Bacteriophage Lysins: the Ultimate EnzybioticEnzybiotics. John Wiley & Sons, Inc., Hoboken, N.J., USA Fogel, M. R.; Gray, G. M. Starch hydrolysis in man: an intraluminal process not requiring membrane digestion. *J Appl Physiol* 1973, 35 (2), 263-267.

Frese, S. A.; Hutkins, R. W.; Walter, J. Comparison of the Colonization Ability of Autochthonous and Allochthonous Strains of Lactobacilli in the Human Gastrointestinal Tract. *Advances in Microbiology* 2012, 02 (03), 399-409 DOI: 10.4236/aim.2012.23051.

Gibson D G, Young L, Chuang R-Y, Venter J C, Hutchison C A, Smith H O. 2009. Enzymatic assembly of DNA molecules up to several hundred kilobases. Nat Meth 6:343-345.

Good L, Stach J E. Synthetic RNA silencing in bacteria—antimicrobial discovery and resistance breaking. Front Microbiol. 2011 Sep. 12; 2:185.

Gomaa A A, Klumpe H E, Luo M L, Selle K, Barrangou R, Beisel C L. 2014. Programmable Removal of Bacterial Strains by Use of Genome-Targeting CRISPR-Cas Systems. mBio 5:e00928-13.

Green et al., Molecular Cloning: A Laboratory Manual, 4th ed., Cold Spring Harbor Laboratory Press, 2012.

Guimarães, V. D.; Gabriel, J. E.; Lefèvre, F.; Cabanes, D.; Gruss, A.; Cossart, P.; Azevedo, V.; Langella, P. Internalin-expressing *Lactococcus lactis* is able to invade small intestine of guinea pigs and deliver DNA into mammalian epithelial cells. *Microbes Infect* 2005, 7 (5-6), 836-844 DOI: 10.1016/j.micinf.2005.02.012.

Guimarães V, Innocentin S, Chatel J-M, Lefèvre F, Langella P, Azevedo V, 582 Miyoshi A. 2009. A new plasmid vector for DNA delivery using lactococci. Genet Vaccines Ther 7:4.

Jacobs C, Huang L J, Bartowsky E, Normark S, Park J T. Bacterial cell wall recycling provides cytosolic muropeptides as effectors for beta-lactamase induction. *EMBO J.* 1994 Oct. 3; 13(19):4684-94.

Jacobs C, Joris B, Jamin M, Klarsov K, Van Beeumen J, Mengin-Lecreulx D, van Heijenoort J, Park J T, Normark S, Frère J M. AmpD, essential for both beta-lactamase regulation and cell wall recycling, is a novel cytosolic N-acetylmuramyl-L-alanine amidase. *Mol Microbiol.* 1995 February; 15(3):553-9.

Kommineni S, Bretl D J, Lam V, Chakraborty R, Hayward M, Simpson P, Cao Y, Bousounis P, Kristich C J, Salzman N H. 2015. Bacteriocin production augments niche competition by enterococci in the mammalian GI tract. Nature 526:719-722.

Lecuit, M.; Ohayon, H.; Braun, L.; Mengaud, J.; Cossart, P. Internalin of *Listeria monocytogenes* with an intact leucine-rich repeat region is sufficient to promote internalization. *Infect Immun* 1997, 65 (12), 5309-5319.

Liu, Y.; Fatheree, N. Y.; Mangalat, N.; Rhoads, J. M. Human-derived probiotic *Lactobacillus reuteri* strains differentially reduce intestinal inflammation. *Am J Physiol Gastrointest Liver Physiol* 2010, 299 (5), G1087-G1096 DOI: 10.1152/ajpgi.00124.2010.

López R, Garcia E, Garcia P, Garcia J L. The pneumococcal cell wall degrading enzymes: a modular design to create new lysins? *Microb Drug Resist.* 1997; 3(2):199-211.

Loessner M J. Bacteriophage endolysins—current state of research and applications. *Curr Opin Microbiol.* 2005 August; 8(4):480-7.

Loessner M J, Kramer K, Ebel F, Scherer S. C-terminal domains of *Listeria monocytogenes* bacteriophage murein hydrolases determine specific recognition and high-affinity binding to bacterial cell wall carbohydrates. *Mol Microbiol.* 2002 April; 44(2):335-49.

Navarre W W, Ton-That H, Faull K F, Schneewind O. 1999. Multiple Enzymatic Activities of the Murein Hydrolase from Staphylococcal Phage φ11. *Journal of Biological Chemistry* 274:15847-15856.

Nelson D, Schuch R, Chahales P, Zhu S, Fischetti V A. 2006. PlyC: A multimeric bacteriophage lysin. Proc Natl Acad Sci USA 103:10765-10770.

Nicoletti M, Bertani G. 1983. DNA fusion product of phage P2 with plasmid pBR322: A new phasmid. Mol Gen Genet 189:343-347.

Oh, P. L.; Benson, A. K.; Peterson, D. A.; Patil, P. B.; Moriyama, E. N.; Roos, S.; Walter, J. Diversification of the gut symbiont *Lactobacillus reuteri* as a result of host-driven evolution. *ISME J* 2010, 4 (3), 377-387 DOI: 10.1038/ismej.2009.123.

Oh J H, van Pijkeren J P. CRISPR-Cas9-assisted recombineering in *Lactobacillus reuteri. Nucleic Acids Res.* 2014; 42(17):e131.

Paez-Espino D, Morovic W, Sun C L, Thomas B C, Ueda K-I, Stahl B, Barrangou R, Banfield J F. 2013. Strong bias in the bacterial CRISPR elements that confer immunity to phage. Nat Comms 4:1430-1430.

Pálffy, R.; Gardlík, R.; Hodosy, J.; Behuliak, M.; Resko, P.; Radvánsky, J.; Celec, P. Bacteria in gene therapy: bactofection versus alternative gene therapy. *Gene Ther* 2006, 13 (2), 101-105 DOI:10.1038/sj.gt.3302635.

Riboulet-Bisson E, Sturme M H J, Jeffery I B, O'Donnell M M, Neville B A, Forde B M, Claesson M J, Harris H, Gardiner G E, Casey P G, Lawlor P G, O'Toole P W, Ross R P. 2012. Effect of *Lactobacillus salivarius* Bacteriocin Abp118 on the Mouse and Pig Intestinal Microbiota. PLoS ONE 7:e31113.

Riedel, C. U.; Monk, I. R.; Casey, P. G.; Morrissey, D.; O'Sullivan, G. C.; Tangney, M.; Hill, C.; Gahan, C. G. M. Improved luciferase tagging system for *Listeria monocy-* togenes allows real-time monitoring in vivo and in vitro. *Appl Environ Microbiol* 2007, 73 (9), 3091-3094 DOI: 10.1128/AEM.02940-06.

Robert S, Steidler L. 2014. Recombinant *Lactococcus lactis* can make the difference in antigen-specific immune tolerance induction, the Type 1 Diabetes case. Microb Cell Fact 13:S11.

Schaefer L, Auchtung T A, Hermans K E, Whitehead D, Borhan B, Britton R A. 2010. The antimicrobial compound reuterin (3-hydroxypropionaldehyde) induces oxidative stress via interaction with thiol groups. *Microbiology* 156:1589-1599.

Sheehan M M, Stanley E, Fitzgerald G F, van Sinderen D. 1999. Identification and characterization of a lysis module present in a large proportion of bacteriophages infecting *Streptococcus thermophilus*. Appl Environ Microbiol 65:569-577.

Shi, Y.; Yan, Y.; Ji, W.; Bin Du; Meng, X.; Wang, H.; Sun, J. Characterization and determination of holin protein of *Streptococcus suis* bacteriophage SMP in heterologous host. *Virol J* 2012, 9 (1), 70-70 DOI: 10.1186/1743-422X-9-70.

Steidler L, Hans W, Schotte L, Neirynck S, Obermeier F, Falk W, Fiers W, 574 Remaut E. 2000. Treatment of Murine Colitis by *Lactococcus lactis* Secreting Interleukin-10. *Science* 289:1352-1355.

Spinler J K, Taweechotipatr M, Rognerud C L, Ou C N, Tumwasorn S, Versalovic J. 2008. Human-derived probiotic *Lactobacillus reuteri* demonstrate antimicrobial activities targeting diverse enteric bacterial pathogens. Anaerobe 14:166-171.

Sulakvelidze, Alexander; Alavidze, Zemphira; and J. Glenn Morris, Jr. Bacteriophage Therapy. *Antimicrob Agents Chemother.* 2001, 45(3): 649-659).

Summers W C. Bacteriophage therapy. *Annu Rev Microbiol.* 2001; 55:437-51.

Sznol, M.; Lin, S. L.; Bermudes, D.; Zheng, L.-M.; King, I. Use of preferentially replicating bacteria for the treatment of cancer. *Journal of Clinical Investigation* 2000, 105 (8), 1027-1030 DOI:10.1172/JC19818.

Talarico T L, Casas I A, Chung T C, Dobrogosz W J. 1988. Production and isolation of reuterin, a growth inhibitor produced by *Lactobacillus reuteri*. Antimicrob Agents Chemother 32:1854-1858.

Tannock, G. W.; Wilson, C. M.; Loach, D.; Cook, G. M.; Eason, J.; O'Toole, P. W.; Holtrop, G.; Lawley, B. Resource partitioning in relation to cohabitation of *Lactobacillus* species in the mouse forestomach. *ISME J* 2011, 6 (5), 927-938 DOI: 10.1038/ismej.2011.161.

Thomas, C. M.; Hong, T.; van Pijkeren, J. P.; Hemarajata, P.; Trinh, D. V.; Hu, W.; Britton, R. A.; Kalkum, M.; Versalovic, J. Histamine Derived from Probiotic *Lactobacillus reuteri* Suppresses TNF via Modulation of PKA and ERK Signaling. *PLoS ONE* 2012, 7 (2), e31951 DOI:10.1371/journal.pone.0037116.g006.

van Pijkeren, J. P.; Morrissey, D.; Monk, I. R.; Cronin, M.; Rajendran, S.; O'Sullivan, G. C.; Gahan, C. G. M.; Tangney, M. A novel *Listeria monocytogenes*-based DNA delivery system for cancer gene therapy. *Hum. Gene Ther.* 2010, 21 (4), 405-416 DOI: 10.1089/hum.2009.022.

van Pijkeren J P, Britton R A. High efficiency recombineering in lactic acid bacteria. *Nucleic Acids Res.* 2012 May; 40(10):e76.

van Pijkeren J-P, Neoh K M, Sirias D, Findley A S, Britton R A. 2012. Exploring optimization parameters to increase ssDNA recombineering in *Lactococcus lactis* and *Lactobacillus reuteri*. Bioengineered 3:209-217.

van Pijkeren, J. P.; Britton, R. A. Precision genome engineering in lactic acid bacteria. *Microb Cell Fact* 2014, 13 Suppl 1, S10-S10 DOI: 10.1186/1475-2859-13-S1-S10

Wang I N, Smith D L, Young R. 2000. Holins: the protein clocks of bacteriophage infections. Annual Reviews in Microbiology Wells M. et al. *Lactococcus lactis*: high-level expression of tetanus toxin fragment C and protection against lethal challenge. *Mol. Microbiol.*, 8 (1993), pp. 1155-1162.

Zhang Y, Eigenbrot C, Zhou L, Shia S, Li W, Quan C, Tom J, Moran P, Di Lello P, Skelton N J, Kong-Beltran M, Peterson A, Kirchhofer D. Identification of a small peptide that inhibits PCSK9 protein binding to the low density lipoprotein receptor. *J Biol Chem.* 2014 Jan. 10; 289(2):942-55.

Zhou, Y.; Liang, Y.; Lynch, K. H.; Dennis, J. J.; Wishart, D. S. PHAST: A Fast Phage Search Tool. 2011, 39 (suppl), W347-W352 DOI: 10.1093/nar/gkr485.

What is claimed is:

1. A microorganism harboring a recombinant gene, wherein the recombinant gene comprises a maltose-inducible promoter operably connected to a coding sequence of a first biologic, wherein the maltose-inducible promoter comprises a sequence at least about 90% identical to SEQ ID NO:1.

2. The microorganism of claim 1, wherein the first biologic comprises a lytic protein.

3. The microorganism of claim 1, wherein the first biologic comprises a lytic protein selected from the group consisting of a holin and a lysin.

4. The microorganism of claim 1, wherein the microorganism is genetically modified to produce a second biologic and wherein the first biologic effects release of the second biologic.

5. The microorganism of claim 4, wherein the second biologic is selected from the group consisting of a carbohydrate, a polypeptide, a nucleic acid, a metabolite, a virus, and a combination thereof.

6. The microorganism of claim 4, wherein the second biologic is a polypeptide produced from a recombinant gene.

7. The microorganism of claim 1, wherein the first biologic comprises a polypeptide comprising a signal sequence.

8. The microorganism of claim 1, wherein the first biologic comprises an RNA.

9. The microorganism of claim 1, wherein the microorganism comprises a member of lactic acid bacteria.

* * * * *

SEQUENCE LISTING

```
<160> NUMBER OF SEQ ID NOS: 2

<210> SEQ ID NO 1
<211> LENGTH: 311
<212> TYPE: DNA
<213> ORGANISM: Lactobacillus reuteri

<400> SEQUENCE: 1
taccaagaat aactttcatc gtaaaaggca agtaattgag gaaacttgaa gtttttctct    60
attacttgcc ttctttattt tattaagcta aatatgtttt aaataattaa ctataacgga   120
cctgcttggc ggaaactaaa cagtaagaac tttaaattat aaaaatctgc aaccgttttc   180
taaaattttg cgcaagcggt tgcgcaaaat tttaaattt gatattatta atattgcaat    240
aattcatgaa gcgcttacaa taatcacaag tgtctttag aactatttta taagttaagg    300
agttgttagc a                                                        311

<210> SEQ ID NO 2
<211> LENGTH: 6500
```

<212> TYPE: DNA
<213> ORGANISM: Artificial Sequence
<220> FEATURE:
<223> OTHER INFORMATION: Extrachromosomal plasmid

<400> SEQUENCE: 2

| | | | | | |
|---|---|---|---|---|---|
| taatctagac | tcgaggaatt | cggtaccccg | ggttcgaagg | cgccaagctt | caaattacag | 60 |
| cacgtgttgc | tttgattgat | agccaaaaag | cagcagttga | taaagcaatt | actgatattg | 120 |
| ctgaaaaatt | gtaatttata | aataaaaatc | accttttaga | ggtggttttt | ttatttataa | 180 |
| attattcgtt | tgatttcgct | ttcgatagaa | caatcaaagc | gagaataagg | aagataaatc | 240 |
| ccataagggc | gggagcagaa | tgtccgagac | taattcatga | gatcgatttt | ttattaaaac | 300 |
| gtctcaaaat | cgtttctgag | acgttttagc | gtttatttcg | tttagttatc | ggcataatcg | 360 |
| ttaaaacagg | cgttatcgta | gcgtaaaagc | ccttgagcgt | agcgtgcttt | gcagcgaaga | 420 |
| tgttgtctgt | tagattatga | aagccgatga | ctgaatgaaa | taataagcgc | agcgtccttc | 480 |
| tatttcggtt | ggaggaggct | caagggagtt | tgagggaatg | aaattccctc | atgggtttga | 540 |
| ttttaaaaat | tgcttgcaat | tttgccgagc | ggtagcgctg | aaaaattttt | tgaaaaaaat | 600 |
| ttggaatttg | gaaaaaaatg | gggggaaagg | aagcgaattt | tgcttccgta | ctacgacccc | 660 |
| ccattaagtg | ccgagtgcca | attttttgtgc | caaaaacgct | ctatcccaac | tggctcaagg | 720 |
| gtttgagggg | ttttttcaatc | gccaacgaat | cgccaacgtt | ttcgccaacg | ttttttataa | 780 |
| atctatattt | aagtagcttt | attgttgttt | ttatgattac | aaagtgatac | actaatttta | 840 |
| taaaattatt | tgattggagt | tttttaaatg | gtgatttcag | aatcgaaaaa | aagagttatg | 900 |
| atttctctga | caaaagagca | agataaaaaa | ttaacagata | tggcgaaaca | aaaaggtttt | 960 |
| tcaaaatctg | cggttgcggc | gttagctata | gaagaatatg | caagaaagga | atcagaataa | 1020 |
| aaaaaataag | cgaaagctcg | cgttttttaga | aggatacgag | ttttcgctac | ttgttttga | 1080 |
| taaggtaata | tatcatggct | attaaatact | aaagctagaa | attttggatt | tttattatat | 1140 |
| cctgactcaa | ttcctaatga | ttggaaagaa | aaattagaga | gtttgggcgt | atctatggct | 1200 |
| gtcagtcctt | tacacgatat | ggacgaaaaa | aaagataaag | atacatggaa | tagtagtgat | 1260 |
| gttatacgaa | atggaaagca | ctataaaaaa | ccacactatc | acgttatata | tattgcacga | 1320 |
| aatcctgtaa | caatagaaag | cgttaggaac | aagattaagc | gaaaattggg | gaatagttca | 1380 |
| gttgctcatg | ttgagatact | tgattatatc | aaaggttcat | atgaatattt | gactcatgaa | 1440 |
| tcaaaggacg | ctattgctaa | gaataaacat | atatacgaca | aaaagatat | tttgaacatt | 1500 |
| aatgattttg | atattgaccg | ctatataaca | cttgatgaaa | gccaaaaaag | agaattgaag | 1560 |
| aatttacttt | tagatatagt | ggatgactat | aatttggtaa | atacaaaaga | tttaatggct | 1620 |
| tttattcgcc | ttagggagc | ggagtttgga | attttaaata | cgaatgatgt | aaagatatt | 1680 |
| gtttcaacaa | actctagcgc | ctttagatta | tggtttgagg | gcaattatca | gtgtggatat | 1740 |
| agagcaagtt | atgcaaaggt | tcttgatgct | gaaacgggg | aaataaaatg | acaaacaaag | 1800 |
| aaaaagagtt | atttgctgaa | aatgaggaat | taaaaaaaga | aattaaggac | ttaaaagagc | 1860 |
| gtattgaaag | atacagagaa | atggaagttg | aattaagtac | aacaatagat | ttattgagag | 1920 |
| gagggattat | tgaataaata | aaagccccccc | tgacgaaagt | cgaggggggc | ttttattttg | 1980 |
| gtttgatgtt | gcgattaata | gcaatacgat | tgcaataaac | aaaatgatcc | ccttagaagc | 2040 |
| aaacttaaga | gtgtgttgat | agtgcattat | cttaaaattt | tgtataatag | gaattgaagt | 2100 |
| taaattagat | gctaaaaata | ggaattgaag | ttaaattaga | tgctaaaaat | ttgtaattaa | 2160 |

```
gaaggaggga ttcgtcatgt tggtattcca aatgcgtaat gtagataaaa catctactgt    2220
tttgaaacag actaaaaaca gtgattacgc agataaataa atacgttaga ttaattccta    2280
ccagtgacta atcttatgac tttttaaaca gataactaaa attacaaaca aatcgtttaa    2340
cttcaggaga gattacatga acaaaaatat aaatatctca aacttttaa cgagtgaaaa    2400 agtactcaac caaataataa aacaattgaa tttaaaagaa accgataccg tttacgaaat    2460
tggaacaggt aaagggcatt taacgacgaa actggctaaa ataagtaaac aggtaacgtc    2520
tattgaatta gacagtcatc tattcaactt atcgtcagaa aaattaaaac tgaatactcg    2580
tgtcacttta attcaccaag atattctaca gtttcaattc cctaacaaac agaggtataa    2640
aattgttggg aatattcctt acaatttaag cacacaaatt attaaaaaag tggtttttga    2700
aagccgtgcg tctgacatct atctgactgt tgaagaagga ttctacaagc gtaccttgga    2760
tattcaccga acactagggt tgctcttgca cactcaagtc tcgattcagc aattgcttaa    2820
gctgccagcg gaatgctttc atcctaaacc aaaagtaaac agtgtcttaa taaaacttac    2880
ccgccatacc acagatgttc cagataaata ttggaagcta tataagtact tgtttcaaa    2940 atgggtcaat cgagaatatc gtcaactgtt tactaaaaat cagtttcgtc aagcaatgaa    3000
acacgccaaa gtaaacaatt taagtaccat tacttatgag caagtattgt ctattttaa    3060 tagttatcta ttatttaacg ggaggaaata attctatgag tcgcttttt aaatttggaa    3120 agttacacgt tactaaaggg aatggagacc ggggtcgacc cttcaataga gttcttaacg    3180
ttaatccgaa aaaactaac gttaatatta aaaataaga tccgcttgtg aattatgtat    3240
aatttgatta gactaaagaa taggagaaag tatgatgata tttaaaaaac tttctcgtta    3300
agataggttg ttggtgagca tgttatatac ggatgtatcg gtttccttaa tgcaaaattt    3360
tgttgctatc ttattaattt ttctattata tagatatatt caagaaaga taacatttaa    3420 acggatcata ttagatattt taatagcgat tattttttca atattatatc tgtttatttc    3480
agatgcgtca ttacttgtaa tggtattaat gcgattaggg tggcattttc atcaacaaaa    3540
agaaaataag ataaaaacga ctgatacagc taatttaatt ctaattatcg tgatccagtt    3600
attgttagtt gcggttggga ctattattag tcagtttacc atatcgatta tcaaaagtga    3660
tttcagccaa aatatattga acaatagtgc aacagatata actttattag gtattttctt    3720
tgctgtttta tttgacggct tgttctttat attattgaag aataagcgga ctgaattaca    3780
acatttaaat caagaaatca ttgaattttc gttagaaaaa caatatttta tatttatatt    3840
tatttatttt atagtaatag aaattatttt agcagttggg aatcttcaag gagtaacagc    3900
cacgatatta ttaaccatta tcattatttt ttgtgtccct atcgggatga ctttttggca    3960
agtgatgctt tttttgaagg cttattcgat tcgccaagaa gccaatgacc aattggtccg    4020
gaatcaacaa cttcaagatt atctagtcaa tatcgaacag cagtacaccg aattacggcg    4080
atttaagcat gattatcaaa acatcttatt atcgttggag agttttgccg aaaagggcga    4140
tcagcaacag tttaaggcgt attaccaaga attattagca caacgccaa ttcaaagtga    4200 aatccaaggg gcagtcattg cacaactcga ctacttgaaa aatgatccta ttcgaggatt    4260
agtcattcaa aagttttttgg cagccaaaca ggctggtgtt actttaaaat tcgaaatgac    4320
cgaaccaatc gaattagcaa ccgctaatct attaacggtt attcggatta tcggtatttt    4380
attagacaat gcgattgaac aagccgttca agaaaccgat caattggtga ttgtgctttt    4440
cttacaatct gatggtttaa tcgaaattac gattgaaaat acggccagtc aagttaagaa    4500
tctccaagca ttttcagagt taggctattc aacgaaaggc gctggtcggg ggactggttt    4560
```

```
agctaatgtg caggatttga ttgccaaaca aaccaattta ttcttagaaa cacagattga    4620
aaatagaaag ttacgacaga cattgatgat tacggaggaa acttaatttg tatcccgttt    4680
atttattaga ggatgattta cagcaacaag cgatttatca gcaaattatc gcgaatacga    4740
ttatgattaa cgaatttgca atgactttaa catgcgctgc cagtgatact gagacattgt    4800
tggcggcaat taaggatcag caacgaggtt tattctttt ggatatggaa attgaggata     4860
accgccaagc cggtttagaa gtggcaacta agattcggca gatgatgccg tttgcgcaaa    4920
ttgtcttcat tacaacccac gaggaactga cattattaac gttagaacga aaaatagcgc    4980
ctttagatta cattctcaag gaccaaacaa tggctgaaat caaaaggcaa ttgattgatg    5040
atctattgtt agctgagaag caaaacgagg cggcagcgta tcaccgagaa aatttattta    5100
gttataaaat aggtcctcgc tttttctcat taccattaaa ggaagttgtt tatttatata    5160
ctgaaaaaga aaatccgggt catattaatt tgttagccgt taccagaaag gttacttttc    5220
caggaaattt aaatgcgctg gaagcccaat atccaatgct ctttcggtgt gataaaagtt    5280
acttagttaa cctatctaat attgccaatt atgacagtaa aacacggagt ttaaatttg     5340 tagatggcag tgaggcaaaa gtctcgttcc ggaaatcacg ggaactagtg gccaaattaa    5400
aacaaatgat gtagcgcctg caggcacgcc aaatgatccc agtaaaaagc cacccgcatg    5460
gcgggtggct ttttattagc cctagaaggg cttcccacac gcatttcagc gccttagtgc    5520
cttagtttgt gaatcatagg tggtatagtc ccgaaatacc cgtctaagga attgtcagat    5580
aggcctaatg actggctttt ataatatgag ataatgccga ctgtactttt tacagtcggt    5640
tttctaatgt cactaacctg ccccgttagt tgaagaaggt ttttatatta cagctccaga    5700
tctaccggtt taatttgaaa attgatatta gcgtttaaca gttaaattaa tacgttaata    5760 attttttgt ctttaaatag ggatttgaag cataatggtg ttatagcgta cttagctggc     5820
cagcatatat gtattctata aaatactatt actaccaaga ataactttca tcgtaaaagg    5880
caagtaattg aggaaacttg aagttttct ctattacttg ccttctttat tttattaagc     5940
taaatatgtt ttaataatt aactataacg gacctgcttg gcggaaacta acagtaaga     6000 actttaaatt ataaaaatct gcaaccgttt tctaaaattt tgcgcaagcg gttgcgcaaa    6060 attttaaat ttgatattat taatattgca ataattcatg aagcgcttac aataatcaca    6120
agtgtctttt agaactattt tataagttaa ggagttgtta gcaatgcaaa caatgcactt    6180
cttacttgca atggctccac ccccgtatca tcaacagtat tttcagcatt ttcaaggaat    6240
ggaagataac tggataatat ggcttttcgt gtgggtaatt atcattgaca taataacagg    6300
gacggcaagg agtttagtaa cgcatcatac aacatcaact aaaggcacat caggcttaat    6360
caagcatggc atcctattaa taataatcct gacgctttat ccaatgcttg atattaatgg    6420
tatgaaaagc gccggcgata cctttacgat gtttttatgta ttattctatg ctgtttcaat    6480
aattgagaat tgcggacaaa                                                6500
```